United States Patent
DeLuca et al.

(10) Patent No.: US 8,232,263 B2
(45) Date of Patent: *Jul. 31, 2012

(54) 17,20(Z)-DEHYDRO VITAMIN D ANALOGS AND THEIR USES

(75) Inventors: Hector F. DeLuca, Deerfield, WI (US); Bulli Padmaja Tadi, Madison, WI (US); Lori A. Plum, Arena, WI (US); Margaret Clagett-Dame, Deerfield, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/775,061

(22) Filed: Jul. 9, 2007

(65) Prior Publication Data

US 2007/0259838 A1    Nov. 8, 2007

Related U.S. Application Data

(63) Continuation of application No. 11/283,090, filed on Nov. 18, 2005, now Pat. No. 7,241,748.

(60) Provisional application No. 60/630,007, filed on Nov. 22, 2004.

(51) Int. Cl.
*A61K 31/59* (2006.01)
*C07D 401/00* (2006.01)

(52) U.S. Cl. ........................ 514/167; 552/653

(58) Field of Classification Search .................. 514/167; 552/653
See application file for complete search history.

(56) References Cited

U.S. PATENT DOCUMENTS

| | | | |
|---|---|---|---|
| 4,666,634 A | 5/1987 | Miyamoto et al. |
| 5,086,191 A | 2/1992 | DeLuca et al. |
| 5,536,713 A | 7/1996 | DeLuca et al. |
| 5,545,633 A | 8/1996 | Bretting |
| 5,585,369 A | 12/1996 | DeLuca et al. |
| 5,843,928 A | 12/1998 | DeLuca et al. |
| 5,929,056 A | 7/1999 | Mourino et al. |
| 5,945,410 A | 8/1999 | DeLuca et al. |
| 6,316,642 B1 | 11/2001 | DeLuca et al. |
| 6,399,797 B1 | 6/2002 | Von Daehne et al. |
| 6,537,981 B2 | 3/2003 | DeLuca et al. |
| 6,566,352 B1 | 5/2003 | DeLuca et al. |
| 6,579,861 B2 | 6/2003 | DeLuca et al. |
| 6,627,622 B2 | 9/2003 | DeLuca et al. |
| 6,846,811 B2 | 1/2005 | DeLuca et al. |
| 6,939,868 B2 | 9/2005 | DeLuca et al. |

(Continued)

FOREIGN PATENT DOCUMENTS

| WO | WO 94/01398 | 1/1994 |
|---|---|---|
| WO | WO 98/24762 | 6/1998 |
| WO | WO 99/18070 | 4/1999 |
| WO | WO 2005/051323 | 6/2005 |

*Primary Examiner* — Sabiha Qazi

(74) *Attorney, Agent, or Firm* — Andrus, Sceales, Starke & Sawall, LLP

(57) ABSTRACT

This invention discloses 17,20(Z)-dehydro vitamin D analogs, and specifically 17(Z)-1α,25-dihydroxy-17(20)-dehydro-2-methylene-19-nor-vitamin $D_3$ and pharmaceutical uses therefor. This compound exhibits pronounced activity in arresting the proliferation of undifferentiated cells and inducing their differentiation to the monocyte thus evidencing use as an anti-cancer agent and for the treatment of skin diseases such as psoriasis as well as skin conditions such as wrinkles, slack skin, dry skin and insufficient sebum secretion. This compound also may be used to treat autoimmune disorders and inflammatory diseases in humans as well as renal osteodystrophy and obesity. This compound also has significant calcemic activity making it a therapeutic agent for the treatment or prophylaxis of osteoporosis, osteomalacia, renal osteodystrophy and hypoparathyroidism.

16 Claims, 5 Drawing Sheets

U.S. PATENT DOCUMENTS

| | | |
|---|---|---|
| 6,992,074 B2 | 1/2006 | DeLuca et al. |
| 7,094,916 B2 | 8/2006 | DeLuca et al. |
| 7,241,748 B2 * | 7/2007 | DeLuca et al. ............ 514/167 |
| 7,241,750 B2 * | 7/2007 | DeLuca et al. ............ 514/167 |
| 7,241,752 B2 * | 7/2007 | DeLuca et al. ............ 514/167 |
| 7,741,313 B2 * | 6/2010 | DeLuca et al. ............ 514/167 |
| 2004/0220418 A1 | 11/2004 | DeLuca et al. |
| 2010/0120728 A1 * | 5/2010 | Petkovich et al. ......... 514/168 |

* cited by examiner

17,20(Z)-DEHYDRO VITAMIN D ANALOGS AND THEIR USES

CROSS REFERENCE TO RELATED APPLICATION

This application is a continuation of U.S. patent application Ser. No. 11/283,090, filed Nov. 18, 2005, now U.S. Pat. No. 7,241,748.

BACKGROUND OF THE INVENTION

This invention relates to vitamin D compounds, and more particularly to 17,20(Z)-dehydro vitamin D analogs and their pharmaceutical uses, and especially 17(Z)-1α,25-dihydroxy-17(20)-dehydro-2-methylene-19-norvitamin $D_3$, its biological activities, and its pharmaceutical uses.

The natural hormone, 1α,25-dihydroxyvitamin $D_3$ and its analog in the ergosterol series, i.e. 1α,25-dihydroxyvitamin $D_2$ are known to be highly potent regulators of calcium homeostasis in animals and humans, and their activity in cellular differentiation has also been established, Ostrem et al., Proc. Natl. Acad. Sci. USA, 84, 2610 (1987). Many structural analogs of these metabolites have been prepared and tested, including 1α-hydroxyvitamin $D_3$, 1α-hydroxyvitamin $D_2$, various side chain homologated vitamins and fluorinated analogs. Some of these compounds exhibit an interesting separation of activities in cell differentiation and calcium regulation. This difference in activity may be useful in the treatment of a variety of diseases such as renal osteodystrophy, vitamin D-resistant rickets, osteoporosis, psoriasis, and certain malignancies.

Another class of vitamin D analogs, i.e. the so called 19-nor-vitamin D compounds, is characterized by the replacement of the A-ring exocyclic methylene group (carbon 19), typical of the vitamin D system, by two hydrogen atoms. Biological testing of such 19-nor-analogs (e.g., 1α,25-dihydroxy-19-nor-vitamin $D_3$) revealed a selective activity profile with high potency in inducing cellular differentiation, and very low calcium mobilizing activity. Thus, these compounds are potentially useful as therapeutic agents for the treatment of malignancies, or the treatment of various skin disorders. Two different methods of synthesis of such 19-nor-vitamin D analogs have been described (Perlman et al., Tetrahedron Lett. 31, 1823 (1990); Perlman et al., Tetrahedron Lett. 32, 7663 (1991), and DeLuca et al., U.S. Pat. No. 5,086,191).

In U.S. Pat. No. 4,666,634, 2β-hydroxy and alkoxy (e.g., ED-71) analogs of 1α,25-dihydroxyvitamin $D_3$ have been described and examined by Chugai group as potential drugs for osteoporosis and as antitumor agents. See also Okano et al., Biochem. Biophys. Res. Commun. 163, 1444 (1989). Other 2-substituted (with hydroxyalkyl, e.g., ED-120, and fluoroalkyl groups) A-ring analogs of 1α,25-dihydroxyvitamin $D_3$ have also been prepared and tested (Miyamoto et al., Chem. Pharm. Bull. 41, 1111 (1993); Nishii et al., Osteoporosis Int. Suppl. 1, 190 (1993); Posner et al., J. Org. Chem. 59, 7855 (1994), and J. Org. Chem. 60, 4617 (1995)).

2-substituted analogs of 1α,25-dihydroxy-19-nor-vitamin $D_3$ have also been synthesized, i.e. compounds substituted at 2-position with hydroxy or alkoxy groups (DeLuca et al., U.S. Pat. No. 5,536,713), with 2-alkyl groups (DeLuca et al U.S. Pat. No. 5,945,410), and with 2-alkylidene groups (DeLuca et al U.S. Pat. No. 5,843,928), which exhibit interesting and selective activity profiles. All these studies indicate that binding sites in vitamin D receptors can accommodate different substituents at C-2 in the synthesized vitamin D analogs.

In a continuing effort to explore the 19-nor class of pharmacologically important vitamin D compounds, analogs which are characterized by the presence of a methylene substituent at carbon 2 (C-2), a hydroxyl group at carbon 1 (C-1), and a shortened side chain attached to carbon 20 (C-20) have also been synthesized and tested. 1α-hydroxy-2-methylene-19-nor-pregnacalciferol is described in U.S. Pat. No. 6,566,352 while 1α-hydroxy-2-methylene-19-nor-homopregnacalciferol is described in U.S. Pat. No. 6,579,861 and 1α-hydroxy-2-methylene-19-nor-bishomopregnacalciferol is described in U.S. Pat. No. 6,627,622. All three of these compounds have relatively high binding activity to vitamin D receptors and relatively high cell differentiation activity, but little if any calcemic activity as compared to 1α,25-dihydroxyvitamin $D_3$. Their biological activities make these compounds excellent candidates for a variety of pharmaceutical uses, as set forth in the '352, '861 and '622 patents.

SUMMARY OF THE INVENTION

The present invention is directed toward 17,20(Z)-dehydro vitamin D analogs, and their pharmaceutical uses, and more specifically toward 17(Z)-1α,25-dihydroxy-17(20)-dehydro-2-methylene-19-norvitamin $D_3$, their biological activity, and various pharmaceutical uses for these compounds.

Structurally these 17,20(Z)-dehydro-vitamin D analogs are characterized by the general formula I shown below:

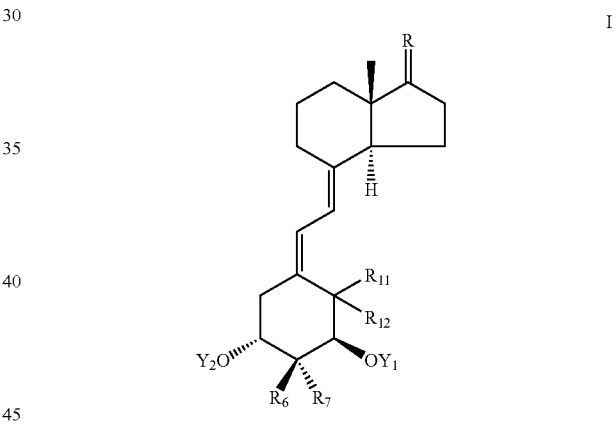

where $Y_1$ and $Y_2$, which may be the same or different, are each selected from the group consisting of hydrogen and a hydroxy-protecting group, where $R_{11}$ and $R_{12}$ are each hydrogen or taken together are a methylene group, where $R_6$ and $R_7$, which may be the same or different, are each selected from the group consisting of hydrogen, alkyl, hydroxyalkyl, fluoroalkyl, hydroxy and alkoxy, or $R_6$ and $R_7$ when taken together may represent the group —$(CH_2)_x$— where x is an integer from 2 to 5, or $R_6$ and $R_7$ when taken together may represent the group $=CR_8R_9$ where $R_8$ and $R_9$, which may be the same or different, are each selected from the group consisting of hydrogen, alkyl, hydroxyalkyl, fluoroalkyl, hydroxy and alkoxy, or when taken together $R_8$ and $R_9$ may represent the group —$(CH_2)_x$— where x is an integer from 2 to 5, and where the group R represents any of the typical side chains known for vitamin D type compounds.

More specifically R can represent a saturated or unsaturated hydrocarbon radical of 1 to 35 carbons, that may be straight-chain, branched or cyclic and that may contain one or more additional substituents, such as hydroxy- or protected-hydroxy groups, fluoro, carbonyl, ester, epoxy, amino or other heteroatomic groups. Preferred side chains of this type are represented by the structure below

where the side chain and 17-ene double bond is in the Z configuration and where Z in the above side chain structure is selected from Y, —OY, —CH$_2$OY, —C≡CY and —CH=CHY, where the double bond in the side chain may have the cis or trans geometry, and where Y is selected from hydrogen, methyl, —COR$^5$ and a radical of the structure:

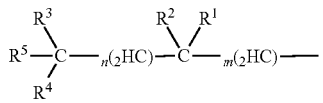

where m and n, independently, represent the integers from 0 to 5, where R$^1$ is selected from hydrogen, deuterium, hydroxy, protected hydroxy, fluoro, trifluoromethyl, and C$_{1-5}$-alkyl, which may be straight chain or branched and, optionally, bear a hydroxy or protected-hydroxy substituent, and where each of R$^2$, R$^3$, and R$^4$, independently, is selected from deuterium, deuteroalkyl, hydrogen, fluoro, trifluoromethyl and C$_{1-5}$ alkyl, which may be straight-chain or branched, and optionally, bear a hydroxy or protected-hydroxy substituent, and where R$^1$ and R$^2$, taken together, represent an oxo group, or an alkylidene group having a general formula C$_k$H$_{2k}$— where k is an integer, the group =CR$^2$R$^3$, or the group —(CH$_2$)$_p$—, where p is an integer from 2 to 5, and where R$^3$ and R$^4$, taken together, represent an oxo group, or the group —(CH$_2$)$_q$—, where q is an integer from 2 to 5, and where R$^5$ represents hydrogen, hydroxy, protected hydroxy, or C$_{1-5}$ alkyl and wherein any of the CH-groups at positions 20, 22, or 23 in the side chain may be replaced by a nitrogen atom, or where any of the groups —CH(CH$_3$)—, —(CH$_2$)$_m$—, —CR$_1$R$_2$— or —(CH$_2$)$_n$— at positions 20, 22, and 23, respectively, may be replaced by an oxygen or sulfur atom.

The preferred analog is 17(Z)-1α,25-dihydroxy-17(20)-dehydro-2-methylene-19-norvitamin D$_3$ which has the following formula Ia:

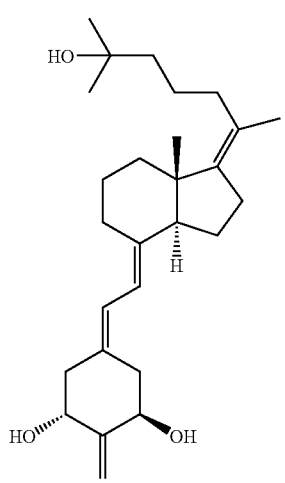

The above compounds of formula I, especially formula Ia, exhibit a desired, and highly advantageous, pattern of biological activity. These compounds are characterized by relatively high binding to vitamin D receptors, as well as relatively high intestinal calcium transport activity, as compared to that of 1α,25-dihydroxyvitamin D$_3$, and they also exhibit relatively high activity in their ability to mobilize calcium from bone, as compared to 1α,25-dihydroxyvitamin D$_3$. Hence, these compounds can be characterized as having relatively high calcemic activity. Their preferential activity on intestinal calcium transport and calcium mobilizing activity allows the in vivo administration of these compounds for the treatment and prophylaxis of metabolic bone diseases. Because of their preferential calcemic activity on gut calcium transport and on bone, these compounds would be preferred therapeutic agents for the treatment and prophylaxis of diseases such as osteoporosis, especially low bone turnover osteoporosis, steroid induced osteoporosis, senile osteoporosis or postmenopausal osteoporosis, as well as osteomalacia and renal osteodystrophy. These analogs having relatively high calcemic activity while being very active on cell differentiation are also expected to be useful as a therapy to treat hypoparathyroidism since they are effective to raise blood calcium levels.

The compounds I, and particularly Ia, of the invention have also been discovered to be especially suited for treatment and prophylaxis of human disorders which are characterized by an imbalance in the immune system, e.g. in autoimmune diseases, including multiple sclerosis, lupus, diabetes mellitus, host versus graft rejection, and rejection of organ transplants; and additionally for the treatment of inflammatory diseases, such as rheumatoid arthritis, asthma, and inflammatory bowel diseases such as celiac disease, ulcerative colitis and Crohn's disease. Acne, alopecia and hypertension are other conditions which may be treated with the compounds of the invention.

The above compounds I, and particularly Ia, are also characterized by relatively high cell differentiation activity. Thus, these compounds also provide therapeutic agents for the treatment of psoriasis, or as an anti-cancer agent, especially against leukemia, colon cancer, breast cancer, skin cancer and prostate cancer. In addition, due to their relatively high cell differentiation activity, these compounds provide therapeutic agents for the treatment of various skin conditions including wrinkles, lack of adequate dermal hydration, i.e. dry skin, lack of adequate skin firmness, i.e. slack skin, and insufficient sebum secretion. Use of these compounds thus not only results in moisturizing of skin but also improves the barrier function of skin.

The compounds of the invention of formula I, and particularly formula Ia, are also useful in preventing or treating obesity, inhibiting adipocyte differentiations, inhibiting SCD-1 gene transcription, and/or reducing body fat in animal subjects. Therefore, in some embodiments, a method of preventing or treating obesity, inhibiting adipocyte differentiations, inhibiting SCD-1 gene transcription, and/or reducing body fat in an animal subject includes administering to the animal subject, an effective amount of one or more of the compounds or a pharmaceutical composition that includes one or more of the compounds of formula I, and in particular the compound of formula Ia. Administration of one or more of the compounds or the pharmaceutical compositions to the subject inhibits adipocyte differentiation, inhibits gene transcription, and/or reduces body fat in the animal subject.

One or more of the compounds may be present in a composition to treat or prevent the above-noted diseases and disorders in an amount from about 0.01 μg/gm to about 1000

μg/gm of the composition, preferably from about 0.1 μg/gm to about 500 μg/gm of the composition, and may be administered topically, transdermally, orally, rectally, nasally, sublingually, or parenterally in dosages of from about 0.01 μg/day to about 1000 μg/day, preferably from about 0.1 μg/day to about 500 μg/day.

BRIEF DESCRIPTION OF THE DRAWINGS

FIG. 1 is a graph illustrating the relative activity of VIT-III and 1,25$(OH)_2D_3$ to compete for binding with [$^3$H]-1,25-$(OH)_2$-$D_3$ to the full-length recombinant rat vitamin D receptor;

FIG. 2 is a graph illustrating the percent HL-60 cell differentiation as a function of the concentration of VIT-III and 1,25$(OH)_2D_3$;

FIG. 3 is a graph illustrating the in vitro transcription activity of 1,25$(OH)_2D_3$ as compared to VIT-III;

FIG. 4 is a bar graph illustrating the bone calcium mobilization activity of 1,25$(OH)_2D_3$ as compared to VIT-III; and FIG. 5 is a bar graph illustrating the intestinal calcium transport activity of 1,25$(OH)_2D_3$ as compared to VIT-III.

DETAILED DESCRIPTION OF THE INVENTION

Figure 1:
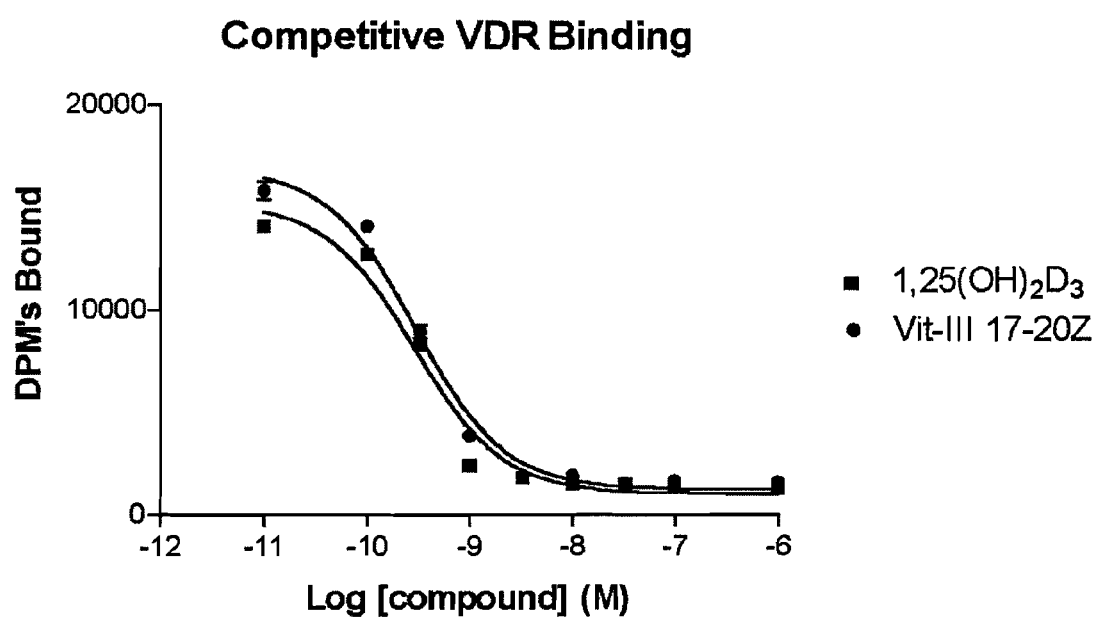
FIGS. 1-5 illustrate various biological activities of 17(Z)-1α,25-dihydroxy-17(20)-dehydro-2-methylene-19-norvitamin $D_3$, hereinafter referred to as "VIT-III," as compared to the native hormone 1α,25-dihydroxyvitamin $D_3$, hereinafter "1,25$(OH)_2D_3$."

The preparation of 17,20(Z)-dehydro vitamin D analogs having the structure I can be accomplished by a common general method, i.e. the condensation of a bicyclic Windaus-Grundmann type ketone II with the allylic phosphine oxide III to the corresponding 17,20(Z)-dehydro vitamin D analog IV followed by deprotection at C-1 and C-3 to provide I:

In the structures III and IV, groups $Y_1$ and $Y_2$ are hydroxy-protecting groups, preferably t-butyldimethylsilyl, it being also understood that any functionalities that might be sensitive, or that interfere with the condensation reaction, be suitably protected as is well-known in the art. The process shown above represents an application of the convergent synthesis concept, which has been applied effectively for the preparation of vitamin D compounds [e.g. Lythgoe et al., J. Chem. Soc. Perkin Trans. I, 590 (1978); Lythgoe, Chem. Soc. Rev. 9, 449 (1983); Toh et al., J. Org. Chem. 48, 1414 (1983); Baggiolini et al., J. Org. Chem. 51, 3098 (1986); Sardina et al,. J. Org. Chem. 51, 1264 (1986); J. Org. Chem. 51, 1269 (1986); DeLuca et al., U.S. Pat. No. 5,086,191; DeLuca et al., U.S. Pat. No. 5,536,713].

The hydrindanones of the general structure II are not known. They can be prepared by the method shown in the Schemes herein (see the preparation of compound VIT-III).

For the preparation of the required phosphine oxides of general structure III, a synthetic route has been developed starting from a methyl quinicate derivative which is easily obtained from commercial (1R,3R,4S,5R)-(−)-quinic acid as described by Perlman et al., Tetrahedron Lett. 32, 7663 (1991) and DeLuca et al., U.S. Pat. No. 5,086,191.

The overall process of the synthesis of compounds I and Ia is illustrated and described more completely in U.S. Pat. No. 5,843,928 entitled "2-Alkylidene-19-Nor-Vitamin D Compounds" the specification of which is specifically incorporated herein by reference.

Particularly preferred 17,20(Z)-dehydro vitamin D analogs are those encompassed by general formula I wherein carbon-2 on the A-ring is substituted with an alkylidene group or an alkyl group, or are hydrolyzable slow release compounds (whether substituted at carbon-2 or not substituted at carbon-2).

2-Alkylidene Compounds

Structurally these 2-alkylidene analogs are characterized by the general formula V shown below:

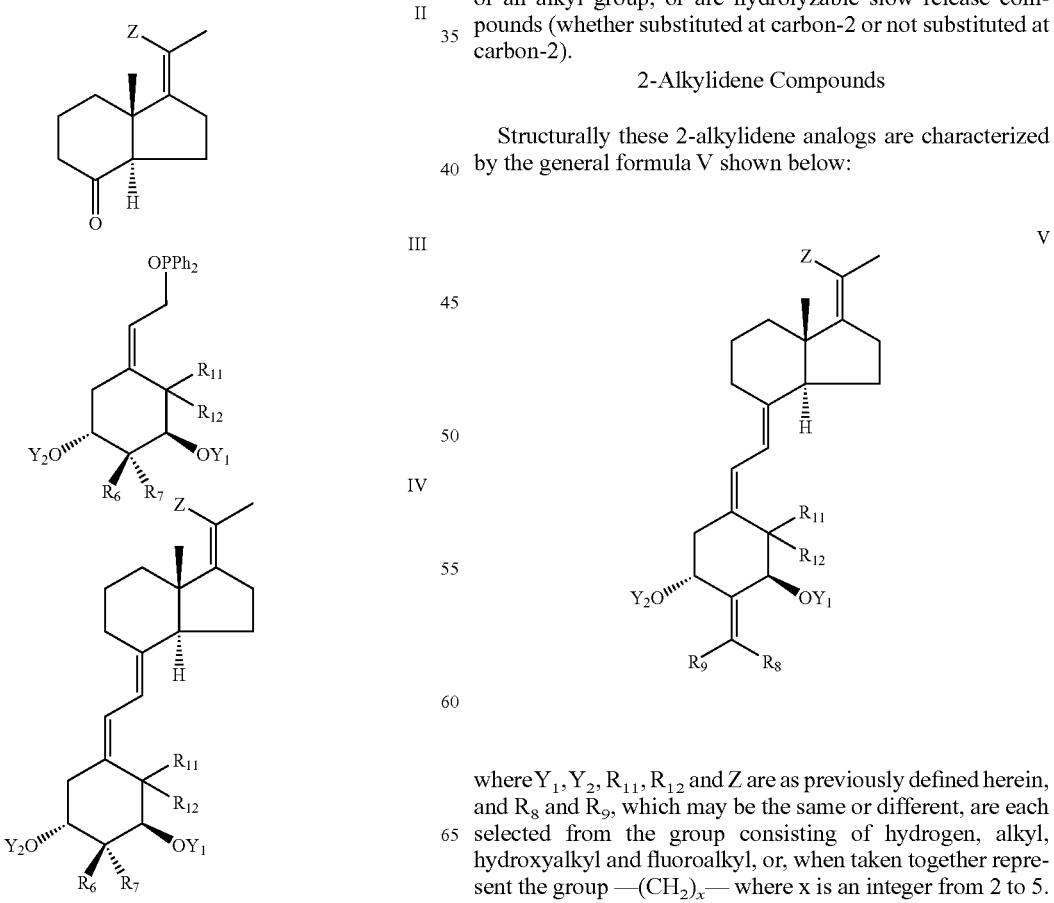

where $Y_1$, $Y_2$, $R_{11}$, $R_{12}$ and Z are as previously defined herein, and $R_8$ and $R_9$, which may be the same or different, are each selected from the group consisting of hydrogen, alkyl, hydroxyalkyl and fluoroalkyl, or, when taken together represent the group —$(CH_2)_x$— where x is an integer from 2 to 5.

2-Alkyl Compounds

Structurally these 2-alkyl analogs are characterized by the general formula VI shown below:

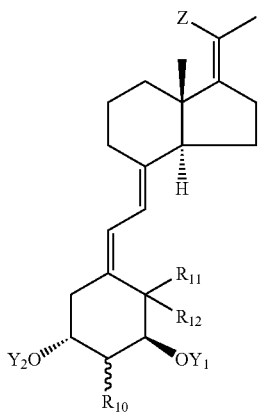

VI where $Y_1$, $Y_2$, $R_{11}$, $R_{12}$ and Z are as previously defined herein, and $R_{10}$ is selected from the group consisting of alkyl, hydroxyalkyl and fluoroalkyl.

Slow Release Compounds

Modified vitamin D compounds that exhibit a desirable and highly advantageous pattern of biological activity in vivo, namely, the more gradual onset and more prolonged duration of activity, may also be used herein.

Structurally, the key feature of the modified vitamin D compounds having these desirable biological attributes is that they are derivatives of 17,20(Z)-dehydro-vitamin D analogs, in which a hydrolyzable group is attached to the hydroxy group at carbon 25 and, optionally, to any other of the hydroxy groups present in the molecule. Depending on various structural factors—e.g. the type, size, structural complexity—of the attached group, these derivatives hydrolyze to the active 17,20(Z)-dehydro-vitamin D analog, at different rates in vivo, thus providing for the "slow release" of the biologically active vitamin D compound in the body.

The "slow release" in vivo activity profiles of such compounds can, of course, be further modulated by the use of mixtures of derivatives or the use of mixtures consisting of one or more vitamin D derivative together with underivatized vitamin D compounds.

It is important to stress that the critical structural feature of the vitamin derivatives identified above is the presence of a hydrolyzable group attached to the hydroxy group at carbon 25 of the molecule. The presence of a hydrolyzable group at that position imparts on the resulting derivatives the desirable "slow-release" biological activity profile mentioned above. Other hydroxy functions occurring in the molecule (e.g. hydroxy functions at carbons 1 or 3) may be present as free hydroxy groups, or one or more of them may also be derivatived with a hydrolyzable group.

The "hydrolyzable group" present in the above-mentioned derivatives is preferably an acyl group, i.e. a group of the type $Q^1CO—$, where $Q^1$ represents hydrogen or a hydrocarbon radical of from 1 to 18 carbons that may be straight chain, cyclic, branched, saturated or unsaturated. Thus, for example, the hydrocarbon radical may be a straight chain or branched alkyl group, or a straight chain or branched alkenyl group with one or more double bonds, or it may be an optionally substituted cycloalkyl or cycloalkenyl group, or an aromatic group, such as substituted or unsubstituted phenyl, benzyl or naphthyl. Especially preferred acyl groups are alkanoyl or alkenoyl groups, of which some typical examples are formyl, acetyl, propanoyl, hexanoyl, isobutyryl, 2-butenoyl, palmitoyl or oleoyl. Another suitable type of hydrolyzable group is the hydrocarbyloxycarbonyl group, i.e. a group of the type $Q^2$-O—CO—, where $Q^2$ is a $C_1$ to $C_{18}$ hydrocarbon radical as defined above. Exemplary of such hydrocarbon radicals are methyl, ethyl, propyl, and higher straight chain or branched alkyl and alkenyl radicals, as well as aromatic hydrocarbon radicals such as phenyl or benzoyl.

These modified vitamin D compounds are hydrolyzable in vivo to the active analog over a period of time following administration, and as a consequence regulate the in vivo availability of the active analog, thereby also modulating their activity profile in vivo. The term "activity profile" refers to the biological response over time of vitamin D compounds. Individual modified compounds, or mixtures of such compounds, can be administered to "fine tune" a desired time course of response.

As used herein the term "modified vitamin D compound" encompasses any vitamin D compound in which one or more of the hydroxy functions present in such a compound are modified by derivatization with a hydrolyzable group. A "hydrolyzable group" is a hydroxy-modifying group that can be hydrolyzed in vivo, so as to regenerate the free hydroxy functions.

In the context of this disclosure, the term hydrolyzable group preferably includes acyl and hydrocarbyloxycarbonyl groups, i.e. groups of the type $Q^1CO—$ and $Q^2$-O—CO, respectively, where $Q^1$ and $Q^2$ have the meaning defining earlier.

Structurally, the modified vitamin D compounds encompassed may be represented by the formula VII shown below:

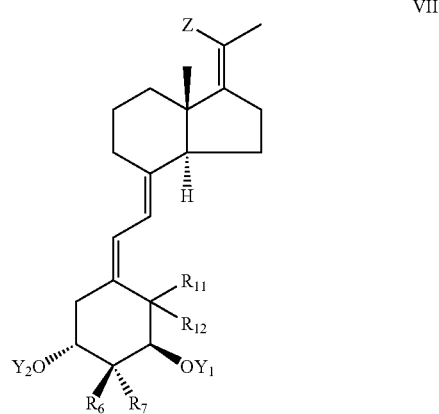

VII where $Y_1$, $Y_2$, $R_{11}$, $R_{12}$, $R_6$, $R_7$ and Z are as previously defined herein with respect to formula I with the exception that $R^5$ in the side chain is $—OY_3$ and $Y_3$ is an acyl group or a hydrocarbyloxycarbonyl group, as previously defined herein.

Some specific examples of such modified vitamin D compounds include 2-substituted derivatives such as:

1,3,25-Triacetates where $Y_1=Y_2=Y_3$ and is $CH_3CO$;
1,3,25-Trihexanoates where $Y_1=Y_2=Y_3$ and is $CH_3(CH_2)_4CO$;
1,3,25-Trinonanoates where $Y_1=Y_2=Y_3$ and is $CH_3(CH_2)_7CO$; and
25-Acetates where $Y_1=Y_2$ and is H and $Y_3$ is $CH_3CO$.

These compounds can be prepared by known methods. See for example WO97/11053 published Mar. 27, 1999, and the previous description herein.

17(Z)-1α,25-dihydroxy-17(20)-dehydro-2-methylene-19-nor-vitamin $D_3$ (referred to herein as VIT-III) was synthesized and tested. Structurally, this 19-nor analog is characterized by the general formula Ia previously illustrated herein.

The preparation of 17(Z)-1α,25-dihydroxy-17(20)-dehydro-2-methylene-19-nor-vitamin $D_3$ having the structure Ia can be accomplished by the condensation of a bicyclic Windaus-Grundmann type ketone IIa with the allylic phosphine oxide IIIa to the corresponding 17(20)-dehydro-vitamin D analog IVa followed by deprotection at C-1 and C-3 to provide Ia:

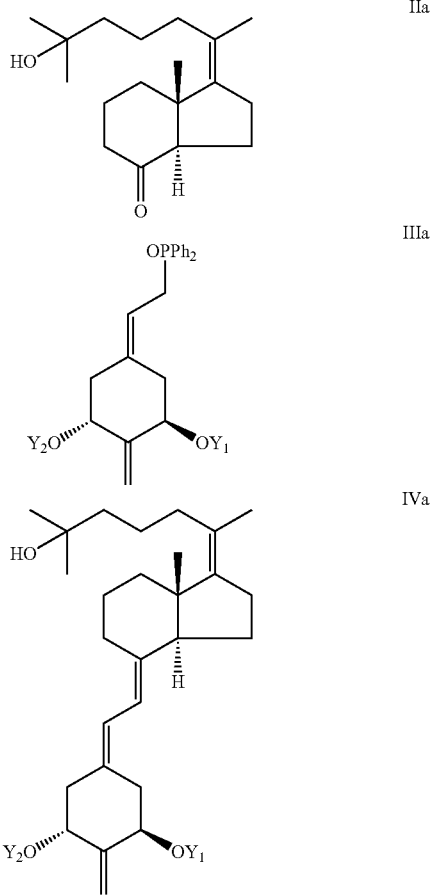

In the structures IIIa and IVa, groups $Y_1$ and $Y_2$ are hydroxy-protecting groups, preferably t-butyldimethylsilyl, it being also understood that any functionalities that might be sensitive, or that interfere with the condensation reaction, be suitably protected as is well-known in the art. The process shown above represents a specific application of the convergent synthesis concept, which was referred to previously herein and has been applied effectively for the preparation of vitamin D compounds The hydrindanone of the general structure IIa is not known. It can be prepared by the method shown in the Schemes herein (see the preparation of compound VIT-III).

As used in the description and in the claims, the term "hydroxy-protecting group" signifies any group commonly used for the temporary protection of hydroxy functions, such as for example, alkoxycarbonyl, acyl, alkylsilyl or alkylarylsilyl groups (hereinafter referred to simply as "silyl" groups), and alkoxyalkyl groups. Alkoxycarbonyl protecting groups are alkyl-O—CO— groupings such as methoxycarbonyl, ethoxycarbonyl, propoxycarbonyl, isopropoxycarbonyl, butoxycarbonyl, isobutoxycarbonyl, tert-butoxycarbonyl, benzyloxycarbonyl or allyloxycarbonyl. The term "acyl" signifies an alkanoyl group of 1 to 6 carbons, in all of its isomeric forms, or a carboxyalkanoyl group of 1 to 6 carbons, such as an oxalyl, malonyl, succinyl, glutaryl group, or an aromatic acyl group such as benzoyl, or a halo, nitro or alkyl substituted benzoyl group. The word "alkyl" as used in the description or the claims, denotes a straight-chain or branched alkyl radical of 1 to 10 carbons, in all its isomeric forms. "Alkoxy" refers to any alkyl radical which is attached by oxygen, i.e. a group represented by "alkyl-o-." Alkoxyalkyl protecting groups are groupings such as methoxymethyl, ethoxymethyl, methoxyethoxymethyl, or tetrahydrofuranyl and tetrahydropyranyl. Preferred silyl-protecting groups are trimethylsilyl, triethylsilyl, t-butyldimethylsilyl, dibutylmethylsilyl, diphenylmethylsilyl, phenyldimethylsilyl, diphenyl-t-butylsilyl and analogous alkylated silyl radicals. The term "aryl" specifies a phenyl-, or an alkyl-, nitro- or halo-substituted phenyl group.

A "protected hydroxy" group is a hydroxy group derivatised or protected by any of the above groups commonly used for the temporary or permanent protection of hydroxy functions, e.g. the silyl, alkoxyalkyl, acyl or alkoxycarbonyl groups, as previously defined. The terms "hydroxyalkyl", "deuteroalkyl" and "fluoroalkyl" refer to an alkyl radical substituted by one or more hydroxy, deuterium or fluoro groups respectively. An "alkylidene" refers to a radical having the general formula $C_kH_{2k}$— where k is an integer.

More specifically, reference should be made to the following description as well as to the Schemes herein for a detailed illustration of the preparation of compound VIT-III.

Synthesis

Des-A,B-23,24-dinorcholan-8β,22-diol (2). A flame dried 1000 mL two necked flask was charged with ergocalciferol 1 (5 g, 12.6 mmol), pyridine (5 mL), and anhydrous MeOH (400 mL). The solution was cooled to −78° C. in an argon atmosphere. $O_3$ was bubbled through the solution until a deep blue color developed and persisted (about 1 h). The solution was treated with $O_2$ until the blue color faded (15 min). Then $NaBH_4$ (1.5 g, 39.7 mmol) was added. After 15 min. second portion of $NaBH_4$ (1.5 g, 39.7 mmol) was added and the reaction was allowed to warm to rt. Then the third portion of $NaBH_4$ (1.5 g, 39.7 mmol) was added and reaction stirred for over night. The reaction was quenched by adding water (50 mL). Methanol was evaporated in vaccuo and residue was dissolved in ethyl acetate. The organic phase was washed with 1N aqueous solution of HCl (100 mL), saturated $NaHCO_3$ solution (100 mL) and brine (100 mL). The organic phase was dried ($Na_2SO_4$), filtered and evaporated. Purification by silica gel chromatography (25% ethyl acetate/hexane) afforded 2.18 g (10.3 mmol, 81%) of diol 2 as a white solid. Mp 110-111° C.; $^1H$ NMR (400 MHz, $CDCl_3$) δ: 0.96 (3H, s), 1.03 (3H, d, J=6.6 Hz), 3.38 (1H, dd, J=10.5, 6.7 Hz), 3.64 (1H, dd, J=10.5, 3.2 Hz), 4.09 (1H, m); $^{13}C$ NMR (100 MHz, $CDCl_3$) δ: 69.2, 67.8, 52.9, 52.4, 41.8, 40.2, 38.2, 33.6, 26.6, 22.6, 17.4, 16.6, 13.6; MS m/z (relative intensity): 212 ($M^+$, 2), 194 ($M^+$-$H_2O$, 15), 179 ($M^+$-$H_2O$—$CH_3$, 18), 125 (43), 111 (100); exact mass calculated for $C_{13}H_{22}O$ $[M-H_2O]^+$ is 194.1671, measured is 194.1665.

Des-A,B-22-(p-toluenesulfonyloxy)-23,24-dinorcholan-8β-ol (3). A solution of diol 2 (1 g, 4.71 mmol) in anhydrous pyridine (12 mL) was cooled to −25° C. and a precooled solution of tosyl chloride (1.08 g, 5.66 mmol) in anhydrous pyridine (2 mL) was added dropwise. The reaction mixture was stirred at that temperature for 4 h and allowed to warm to 0° C. and stirred at that temperature for additional 20 h. The mixture was diluted with $CH_2Cl_2$ (50 mL) and washed with saturated $CuSO_4$ solution (30 mL), 1N HCl (30 mL), and water (50 mL). The organic phase was dried ($Na_2SO_4$), filtered and concentrated. Purification by silica gel chromatography (25% ethyl acetate/hexane) yielded 1.7 g (4.64 mmol, 98%) of tosylate 3. $^1H$ NMR (400 MHz, $CDCl_3$) δ: 0.89 (3H, s), 0.96 (3H, d, J=6.6 Hz), 2.45 (3H, s), 3.8 (1H, dd, J=9.2, 6.2 Hz), 3.95 (1H, dd, J=9.2, 3.0 Hz), 4.06 (1H, m), 7.35 (2H, d, J=8.2 Hz), 7.78 (2H), d, J=8.2 Hz); $^{13}C$ NMR (100 MHz, $CDCl_3$) δ: 144.7, 133.0, 129.8, 127.9, 75.6, 69.0, 60.4, 52.2, 41.9, 40.1, 35.7, 33.5, 26.4, 22.4, 21.6, 17.3, 16.7, 13.4; MS m/z (relative integration): 366 ($M^+$, 6), 194(14), 179(16), 125(30), 111(100); exact mass calculated for $C_{20}H_{30}SO_4Na$ ($M+Na^+$) is 389.1763, measured is 389.1768.

Des-A,B-8β-[(tert-butyldimethylsilyl)oxy]-22-(p-toluenesulfonyloxy)-23,24-dinorcholane (4). To a 0° C. cooled solution of hydroxyl tosylate 3 (1.5 g, 4.09 mmol) in anhydrous DMF (20 mL) was added 2,6-lutidine (0.580 mL, 0.52 g, 4.92 mmol) followed by TBSOTf (1.13 mL, 1.30 g, 4.92 mmol). The solution was stirred at 0° C. for 15 min and water (10 mL) was added. The mixture was extracted with ethyl acetate (3×40 mL), and combined organic phases were washed with 1N aqueous solution of NaOH (40 mL) dried ($Na_2SO_4$), filtered and concentrated. The residue was purified by silica gel column chromatography (5% ethyl acetate/hexane) to give 1.94 g (4.04 mmol, 99%) of 4. $^1H$ NMR (400 MHz, $CDCl_3$) δ: 0.01 (6H, s), 0.88 (12H, s), 0.96 (3H, d, J=6.8 Hz), 2.45 (3H, s), 3.81 (1H, dd, J=9.2, 6.4 Hz), 3.97 (1H, dd, J=9.7, 3.0 Hz), 3.99 (1H, m), 7.34 (2H, d, J=8.08 Hz), 7.79 (2H, d, J=8.2 Hz). $^{13}C$ NMR (100 MHz, $CDCl_3$) δ: 114.5, 133.4, 129.8, 127.9, 74.8, 69.3, 52.3, 52.6, 42.2, 40.5, 35.8, 34.4, 26.6, 25.9, 23.0, 21.6, 18.0, 17.6, 16.8, 13.7, −4.8, −5.1.

Des-A,B-8β-[(tert-butyldimethylsilyl)oxy]-23,24-dinorcholan-22-al (5). A solution of 4 (1.9 g, 3.96 mmol) in DMSO (5 mL) was added to a suspension of $NaHCO_3$ (1.5 g, 17.9 mmol) in DMSO (20 mL) at rt. The mixture was heated to 150° C. under argon for 15 min and cooled to rt. Water (50 mL) followed by ethyl acetate (50 mL) were added and aqueous phase was extracted with ethyl acetate (3×30 mL). The combined organic phases were dried ($Na_2SO_4$), filtered and concentrated. The residue was purified by column chromatography (2% ethyl acetate/hexane) to afford 0.93 g (2.87 mmol, 76%) of aldehyde 5. H NMR (400 MHz, $CDCl_3$) δ: 0.01 (6H, 2s), 0.89 (9H, s), 0.97 (3H, s), 1.09 (3H, d, J=6.8 Hz), 2.35 (1H, m), 4.03 (1H, m), 9.58 (1H, d, J=3.2 Hz). $^{13}C$ NMR (100 MHz, $CDCl_3$) δ: 205.2, 69.1, 52.4, 51.8, 49.1, 42.7, 40.5, 30.8, 34.3, 26.2, 25.8, 23.3, 17.6, 14.1, 13.3, −4.7, −5.1.

Des-A,B-8β-[(tert-butyldimethylsilyl)oxy]-pregnan-20-one (6). A flame dried flask was charged with t-BuOK (1.55 g, 13.9 mmol) and anhydrous t-BuOH (30 mL) at room temperature. $O_2$ was bubbled through the solution for 15 min. A solution of aldehyde 5 (0.9 g, 2.78 mmol) in anhydrous t-BuOH (15 mL) was added to the reaction mixture and $O_2$ was bubbled through the solution for additional 10 min. The reaction was quenched with water (15 mL) and extracted with ether (3×30 mL). The combined organic phases were dried ($Na_2SO_4$), filtered and concentrated. The residue was purified by silica gel column chromatography (3% ethyl acetate/hexane) to give 0.61 g (1.97 mmol, 71%) of the ketone 6. $^1H$ NMR (400 MHz, $CDCl_3$) δ: 0.01 (6H, s), 0.84 (3H, s), 0.87 (9H, s), 2.08 (3H, s), 2.46 (1H, t, J=9.1 Hz), 4.03 (1H, m). $^{13}C$ NMR (100 MHz, $CDCl_3$) δ: 209.5, 69.0, 64.5, 53.2, 43.7, 39.8, 34.2, 31.6, 25.8, 23.2, 21.8, 17.6, 15.5, −4.8, −5.2.

5-Bromo-2-methyl-2-pentanol (8). To a −20° C. cooled solution of ethyl-4-bromobutyrate 7 (5 g, 25.6 mmol) in anhydrous diethyl ether (50 mL) was added 3M solution of methylmagnesium bromide in diethyl ether (17.1 mL, 6.11 g, 51.3 mmol) under argon atmosphere over a period of 30 min. The reaction mixture was stirred at room temperature for overnight. Saturated ammonium chloride solution was added to hydrolyze the reaction mixture followed by 1N HCl solution to dissolve the inorganic salts formed. The aqueous phase was extracted with ether (3×50 mL). The combined extracts were washed with water (100 mL), saturated NaCl solution (100 mL), dried ($Na_2SO_4$), filtered and concentrated. The residue was purified by silica gel column chromatography (20/80 ethyl acetate/hexane) to afford 3.1 g (17.1 mmol, 67%) of tertiary alcohol 8. $^1H$ NMR (400 MHz, $CDCl_3$) δ: 1.27 (6H, s), 1.64 (2H, m), 1.96 (2H, m), 3.44 (2H, t, J=6.68 Hz).

5-Bromo-2methyl-2[(tert-butyldimethylsilyl)oxy]-pentane (9). To a −50° C. cooled solution of alcohol 8 (3 g, 16.6 mmol) in anhydrous $CH_2Cl_2$ (50 mL) was added 2,6-lutidine (2.32 mL, 2.13 g, 19.89 mmol) followed by TBSOTf (4.57 mL, 5.26 g, 19.9 mmol). The solution was stirred at 0° C. for 15 min and water (10 mL) was added. The mixture was extracted with $CH_2Cl_2$ (3×40 mL), and combined organic phases were washed with 1N aqueous solution of NaOH (40 mL), dried ($Na_2SO_4$), filtered and concentrated. The residue was purified by silica gel column chromatography (1% ethyl acetate/hexane) to give 3.9 g (13.2 mmol, 80%) of 9. $^1H$ NMR (400 MHz, $CDCl_3$) δ: 0.07 (6H, s), 0.85 (9H, s), 1.21 (6H, s), 1.55 (2H, m), 1.95 (2H, m), 3.41 (2H, t, J=6.8 Hz)

Des-A,B-cholest-17(20)-dehydro-8β,25-diols (15a and 15b)

A solution of 5-bromo-2methyl-2[(tert-butyldimethylsilyl)oxy]pentane 9 (2.84 g, 9.68 mmol) in anhydrous ether (20 mL, containing catalytic amount of iodine) was added dropwise to a stirred suspension of magnesium powder (0.23 g, 9.68 mmol) in anhydrous diethyl ether (5 mL) at room temperature with occasional warming it up to 35° C. under argon atmosphere. After generation of the Grignard reagent was complete the mixture was stirred for 1 hr at room temperature and for 1 hr at 40° C. Then it was cooled to 0° C. and a solution of ketone 6 (0.6 g, 1.94 mmol) in anhydrous diethyl ether (10 mL) was added dropwise over a period of 30 min. After stirring the reaction mixture at room temperature for 3 h it was hydrolyzed with aqueous solution of $NH_4Cl$ (20 mL). The organic layer was separated and aqueous phase was extracted with ethyl acetate (3×30 mL). The combined organic phases were washed with water (40 mL), dried ($Na_2SO_4$) and evaporated. Silica gel column chromatography of the residue gave 0.95 g (94%) of mixture of alcohols 10. Phosphorous oxychloride (3 mL) was added dropwise to a solution of mixture of alcohols 10 (0.95 g) in anhydrous pyridine (20 mL) under argon atmosphere. The reaction was stirred at room temperature overnight and poured into ice-water and extracted with ether (3×20 mL). The organic layer was washed with saturated $CuSO_4$ solution (30 mL), 1N HCl (30 mL), water (50 mL). The organic phase was dried ($NaSO_4$), filtered and concentrated. Column Chromatography of crude mixture furnished 0.72 g (78%) of mixture of olefins 11a, 11b, 12a, 12b, 13. The olefin mixture without further purification was dissolved in methanol (20 mL) and p-Toluenesulfonic acid monohydrate (p-TSA) (0.100 g) was added at 0° C. The reaction was stirred at room temperature for 3 days [Additional amounts of p-TSA were successively added (100 mg, 24 h; 75 mg, 36 h; 50 mg, 48 h)]. Methanol was evaporated and residue was diluted with ethyl acetate (30 mL). The organic phase was washed with saturated aqueous $NaHCO_3$ solution (20 mL) water (20 mL), dried ($Na_2CO_3$) and evaporated. The residue was purified on column chromatography to yield 0.284 g (79%) of mixture of olefin alcohols 14a, 14b, 15a, 15b, 16. The olefin alcohols were separated on HPLC.

17(E)-Des-A,B-cholestan-17(20)-dehydro-8β,25-diol (15a). The olefin alcohols were separated on HPLC (9.4 mm×25 cm zorbax-sil column, 4 ml/min) using IPA/hexane (4/96) solvent system. Pure diol 17-20E 15a 70 mg (250 μmol, 25%) was eluted at Rv=50 mL. $[\alpha]^{25}_D$-16.5° (c 1.02, $CHCl_3$); $^1$H NMR (400 MHz, $CDCl_3$) δ: 1.09 (3H, s), 1.20 (6H, s), 1.67 (3H, t, J=1.84 Hz), 4.14 (1H, m). $^{13}$C NMR (100 MHz, $CDCl_3$) δ: 143.2, 123.7, 71.0, 69.8, 52.4, 43.9, 43.7, 38.3, 36.8, 33.4, 29.2, 28.5, 23.5, 22.2, 19.1, 17.9, 17.2. MS m/z (relative intensity): 280 ($M^+$, 16), 262 ($M-H_2O^+$, 7), 229 ($M-2\times H_2O-CH_3^+$, 16) 179(54), 161(100); Exact mass calculated for $C_{18}H_{32}O_2$ $[M+Na]^+$ is 303.2300, found 303.2297.

17(E)-25-(Triethylsilyloxy)-des-A,B-cholestan-17(20)-dehydro-8-one (17a). To a solution of alcohol 15a (20 mg, 71 μmol) in anhydrous $CH_2Cl_2$ (5 mL) was added PDC (40 mg, 107 μmol) at rt. After stirring the reaction for 3 h under argon atmosphere the solution was passed through a pad of celite with ethyl acetate. The filtrate was concentrated and applied on a Sep-Pak cartridge and eluted with ethyl acetate/hexane (20/80) to give 17 mg, (61.1 μmol, 86%) of ketone as colorless oil. To a −50° C. cooled solution of ketone (17 mg, 61.1 μmol) in anhydrous $CH_2Cl_2$ (5 mL) was added 2,6-lutidine (9 μL, 7.86 mg, 73.3 μmol) followed by TESOTf (17 μL, 19.4 mg, 73.3 μmol). The solution was stirred at 0° C. for 15 min and water (5 mL) was added. The mixture was extracted with $CH_2Cl_2$ (3×5 mL), and combined organic phases were dried ($Na_2SO_4$), filtered and concentrated. The ketone was purified on HPLC (9.4-mm×25-cm Zorbax-Sil column, 4 ml/min) using 10% ethyl acetate/hexane solvent system. Pure ketone 17a 14.4 mg (36.7 μmol, 60%) was eluted at $R_v$=20 mL as colorless oil. $[\alpha]^{25}_D$-14.4 (c 0.73, $CHCl_3$); $^1$H NMR (400 MHz, $CDCl_3$) δ: 0.56 (6H, q, J=7.7 Hz), 0.84 (3H, s), 0.94 (9H, t, J=4.76 Hz), 1.18 (6H, s), 1.71 (3H, t, J=1.84 Hz), 2.57 (1H, dd, J=12, 6.2 Hz). $^{13}$C NMR (100 MHz, $CDCl_3$) δ: 212.2, 141.2, 126.1, 73.3, 61.8, 50.5, 44.7, 40.6, 36.9, 36.7, 29.9, 29.8, 28.7, 23.9, 22.1, 20.2, 17.8, 17.6, 7.1, 6.8. MS m/z (relative intensity): No $M^+$, 377($[M-CH_3]^+$, 3) 363($[M-C_2H_5]^+$, 9), 204(100), 189((18), 161(45). Exact mass calculated for $C_{24}H_{44}O_2Si$ $[M+Na]^+$ is 415.3008, found 415.3016.

17(E)-1α,25 Dihydroxy-17(20)-dehydro-2-methylene-19-norvitamin $D_3$ (20a). To a solution of phosphine oxide 18 (0.051 g, 87.6 μmol) in anhydrous THF (500 μL) at −25° C. was slowly added PhLi 1.2M in cyclohexane/ether (70/30) (80 μL, 8.1 mg, 96.4 μmol) under argon with stirring. The solution turned deep orange. The mixture was stirred at that temperature for 20 min and cooled to −78° C. A precooled (−78° C.) solution of ketone 17a (14 mg, 35.7 μmol) in anhydrous THF (100 μL) was added slowly. The mixture was stirred under argon atmosphere at −78° C. for 3 h and at 0° C. for 18 h. Ethyl acetate was added and organic phase was washed with brine, dried ($Na_2SO_4$) and evaporated. The residue was applied on a Sep-Pak cartridge, and eluted with 1% ethyl acetate/hexane to give 19-nor protected vitamin derivative 19a (8 mg of unreacted ketone 17a was recovered). The protected vitamin was further purified by HPLC (9.4-mm× 25-cm Zorbax-Sil column, 4 ml/min) using hexane/IPA (99.95/0.05) solvent system. Pure compound 19a, 7.7 mg (10.2 μmol, 29%) was eluted at $R_v$=20 mL as colorless oil. UV (in hexane) $\lambda_{max}$ 243.1, 252, 262.2 nm; $^1$H NMR (400 MHz, $CDCl_3$) δ: 0.03, 0.05, 0.07, 0.08 (each 3H, each s), 0.56 (6H, q, J=7.8 Hz), 0.74 (3H, s), 0.87 and 0.91 (each 9H, each s), 0.96 (9H, t, J=7.8 Hz), 1.19 (6H, s), 1.68 (3H, t, J=1.86 Hz), 2.18 (1H, dd, J=12.6, 8.3 Hz), 2.33 (1H, m) 2.46 (1H, dd, 12.6, 4.6 Hz), 2.53 (1H, dd, 13.3, 5.88 Hz), 2.80 (1H, m), 4.43 (2H, m), 4.93 and 4.97 (1H and 1H, each s), 5.88 and 6.21 (1H and 1H, each d, J=11.2 Hz); MS m/z (relative intensity): No $M^+$, 624(59), 366(32), 91(100); Exact mass calculated for $C_{45}H_{84}O_3Si_3$ $[M+Na]^-$ is 779.5626, found 779.5648.

The protected vitamin 19a (7.7 mg, 10.2 μmol) was dissolved in anhydrous THF (500 μL) and treated with TBAF (0.102 mL, 26.7 mg, 102 μmol) and stirred at rt in dark for overnight. The solvent was removed in vaccuo and residue was applied on Sep-Pak cartridge, and eluted with 30% ethyl acetate/hexane to get the deprotected vitamin 20a. The vitamin was further purified by HPLC (9.4-mm×25-cm Zorbax-Sil column, 3 mL/min) using hexane/IPA (90/10) as solvent system. Pure vitamin 20a, 2.9 mg (7 μmol, 69%) was collected at $R_v$=42 mL as white solid: UV (in EtOH) $\lambda_{max}$ 242.9, 251, 261.2 nm; $^1$H NMR (500 MHz, $CDCl_3$) δ: 0.74 (3H, s), 1.22 (6H, s), 1.69 (3H, t, J=1.94 Hz,), 2.29 (1H, dd, J=13.0, 8.39 Hz), 2.32 (1H, dd, J=13.9, 7.0 Hz), 2.57 (1H, dd, J=13.4, 3.49 Hz), 2.79 (1H, br d) 2.87 (1H, dd, J=13.0, 4.59 Hz), 4.49 (2H, m), 5.09 and 5.11 (1H and 1H, each s), 5.92 and 6.35 (1H and 1H, each d, J=11.29 Hz); MS m/z (relative intensity): 414 ($M^+$, 36), 396($[M-H_2O]^+$, 6), 381($[M-H_2O-CH_3]^+$, 8) 285 (70), 149(61), 69(100).

17(Z)-Des-A,B-cholest-17(20)-dehydro-8β,25-diol (15b). The olefin alcohols were separated on HPLC (9.4 mm×25 cm zorbax-sil column, 4 ml/min) using IPA/hexane (5/95) solvent system. Diol 17-20Z 15b and Diol 20-21 16 eluted out together at Rv=45 mL. The alcohols were oxidized together.

17(Z)-25-(Triethylsilyloxy)-des-A,B-cholest-17(20)-dehydro-8-one (17b). To a solution of mixture of alcohols 15b and 16 (34 mg, 121 μmol) in anhydrous $CH_2Cl_2$ (5 mL) was added PDC (55 mg, 145.7 μmol) at rt. After stirring the reaction for 3 h under argon atmosphere the solution was passed through a pad of celite with ethyl acetate. The filtrate was concentrated and applied on a Sep-Pak cartridge and eluted with ethyl acetate/hexane (20/80) to give a mixture of ketones 17b and 16b 30.2 mg (108.6 μmol, 89%) as colorless oil. To a −50° C. cooled solution of ketones 30.2 mg (30.2 mg, 108.6 μmol) in anhydrous $CH_2Cl_2$ (10 mL) was added 2,6-lutidine (16 μL, 13.9 mg, 130.3 μmol) followed by TESOTf (30 μL, 34.5 mg, 130.3 μmol). The solution was stirred at 0° C. for 15 min and water (10 mL) was added. The mixture was extracted with $CH_2Cl_2$ (3×5 mL), and combined organic phases dried ($Na_2SO_4$), filtered and concentrated. The residue was purified by HPLC (9.4-mm×25-cm Zorbax-Sil column, 4 ml/min) using ethyl acetate/hexane (5/95) solvent system. Pure ketone 17b 7.7 mg (19.6 μmol, 18%) was eluted at $R_v$=34 mL as colorless oil. $^1$H NMR (400.13 MHz, $CDCl_3$) δ: 0.56 (6H, q, J=7.78 Hz), 0.83 (3H, s), 0.94 (9H, t, J=7.9 Hz), 1.2 (6H, s), 1.57 (3H, br s), 2.57 (1H, dd, J=11.8, 6.3 Hz); $^{13}$CNMR (100 MHz, $CDCl_3$) δ: 212.18, 141.1, 126.8, 73.2, 62.0, 50.5, 45.3, 40.7, 37.1, 34.5, 29.9, 29.8, 24.0, 23.8, 20.2, 20.1, 18.7, 7.1, 6.8. MS m/z (relative intensity): No $M^+$, 363 ($[M-C_2H_5]^+$, 10), 334 ($[M-2\times C_2H_5]^+$, 1), 204 (100).

17(Z)-1α,25 Dihydroxy-17(20)-dehydro-2-methylene-19-norvitamin $D_3$ (20b). To a solution of phosphine oxide 10 (62 mg, 106.5 μmol) in anhydrous THF (750 μL) at −25° C. was slowly added PhLi 1.8 M in Di-n-butyl ether (59 μL, 8.9 mg, 106.5 μmol) under argon with stirring. The solution turned deep orange. The mixture was stirred at that temperature for 20 min and cooled to −78° C. A precooled (−78° C.) solution of ketone 17b (7.7 mg, 19.6 μmol) in anhydrous THF (100 μL) was added slowly. The mixture was stirred under argon atmosphere at −78° C. for 3 h and at 0° C. for 18 h. Ethyl acetate was added and organic phase was washed with brine, dried (Na₂SO₄) and evaporated. The residue was applied on a Sep-Pak cartridge, and eluted with 1% ethyl acetate/hexane to give the 19-nor protected vitamin derivative. The vitamin was further purified by HPLC (9.4-mm×25-cm Zorbax-Sil column, 4 ml/min) using hexane/IPA (99.95:0.05) solvent system. Pure compound 19b, 12.8 mg (16.9 μmol, 86%) was eluted at $R_v$=19 mL as colorless oil. $[\alpha]^{25}_D$ −9.35 (c 0.64, CHCl₃); UV (in hexane): $\lambda_{max}$244.4, 253.2, 263.2 nm; ¹H NMR (400 MHz, CDCl₃) δ: 0.026, 0.050, 0.067, 0.082 (each 3H, each s), 0.56 (6H, q, J=7.84 Hz), 0.74 (3H, s), 0.86, 0.89 (each 9H, each s), 0.94 (9H, t, J=7.96 Hz), 1.19 (6H, s), 1.56 (3H, br s), 2.14 (1H, dd, J=12.5, 4.8 Hz), 2.33 (1H, dd, J=13.1, 2.8 Hz), 2.46 (1H, dd, J=12.7, 4.4 Hz), 2.53 (1H, dd, J=13.3, 6.0 Hz), 2.80 (1H, br d, J=13.5 Hz), 4.43 (2H, m), 4.92 and 4.97 (each 1H, each s), 5.88 and 6.21 (each 1H, each d, J=11.1 Hz); ¹³C NMR (100 MHz, CDCl₃) δ: 152.9, 142.2, 140.8, 132.8, 125.9, 122.3, 116.3, 106.2, 73.3, 72.5, 71.6, 56.7, 47.6, 46.8, 45.4, 30.1, 29.8, 28.5, 25.8, 25.7, 23.9, 23.6, 23.0, 19.9, 18.2, 18.1, 17.8, 7.1, 6.8, −4.8, −5.0; MS m/z (relative intensity): No M⁺, 366(2), 263(100); Exact mass calculated for C₄₅H₈₄O₃Si₃[M+Na]⁺ is 779.5624, found 779.5647.

The protected vitamin 19b (12.8 mg, 16.9 mmol) was dissolved in anhydrous THF (500 μL) and treated with TBAF (170 μL, 44.2 mg, 169 μmol) and stirred at rt in dark for overnight. The solvent was removed in vaccuo and residue was applied on Sep-Pak cartridge, and eluted with 30% ethyl acetate/hexane to get the deprotected vitamin. The vitamin was further purified by HPLC (9.4-mm×25-cm Zorbax-Sil column, 4 ml/min) using hexane/IPA (85/15) as solvent system. Pure vitamin 20b, 4.3 mg (10.3 μmol, 62%) was eluted at $R_v$=33 mL. UV (in ethanol): $\lambda_{max}$244.1, 252.5, 262.1 nm; ¹H NMR (400 MHz, CDCl₃) δ: 0.74 (3H, s), 1.21 (6H, s), 1.57 (3H, br s), 2.30 (2H, m), 2.57 (1H, dd, J=13.3, 3.6 Hz), 2.79 (1H, dd, J=11.6, 2.52 Hz), 2.85 (1H, dd, J=13.1, 4.44 Hz), 4.48 (2H, m), 5.09 and 5.11 (1H and 1H, each s), 5.92 and 6.35 (1H and 1H, each d, J=11.3 Hz); MS m/z (relative intensity):414 (M⁺, 90), 399 (M-CH₃⁺, 17), 381 [M-CH₃—H₂O]⁺, 18), 363 ([M-CH₃-2×H₂O]⁺, 7), 285 (86), 243 (35), 91 (100); exact mass calculated for C₂₇H₄₂O₃ ([M+Na]⁺) is 437.3032, measured is 437.3026.

Schemes

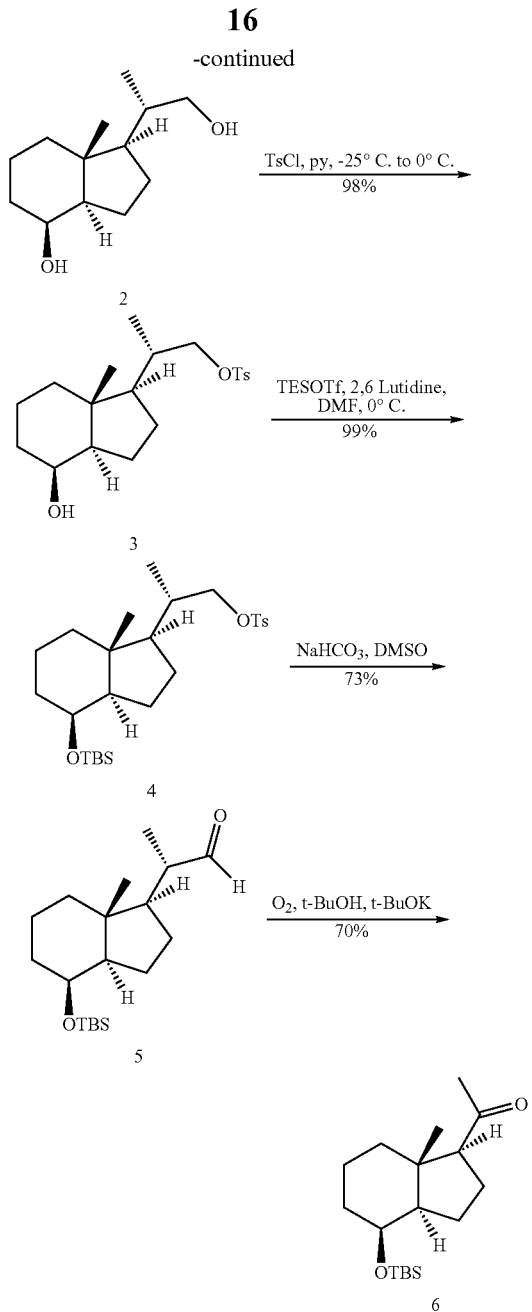

Scheme - I

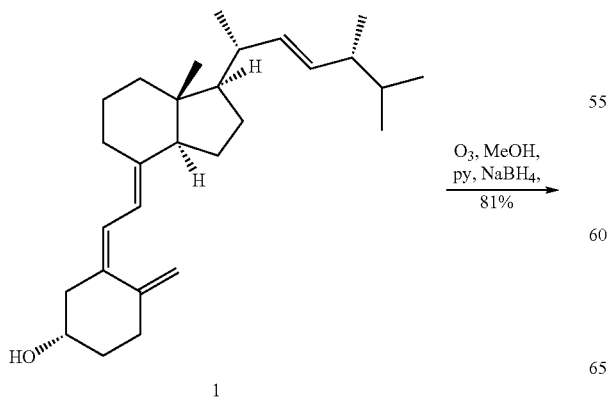

Scheme - II

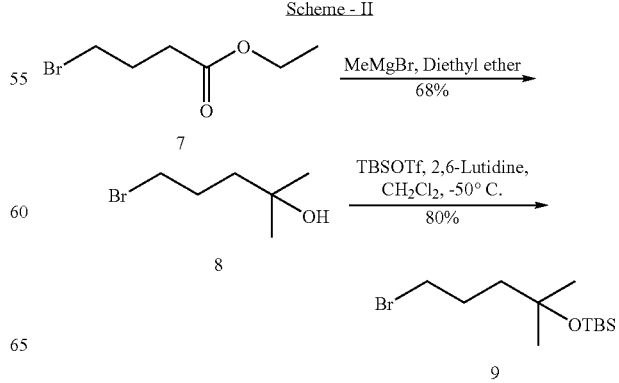

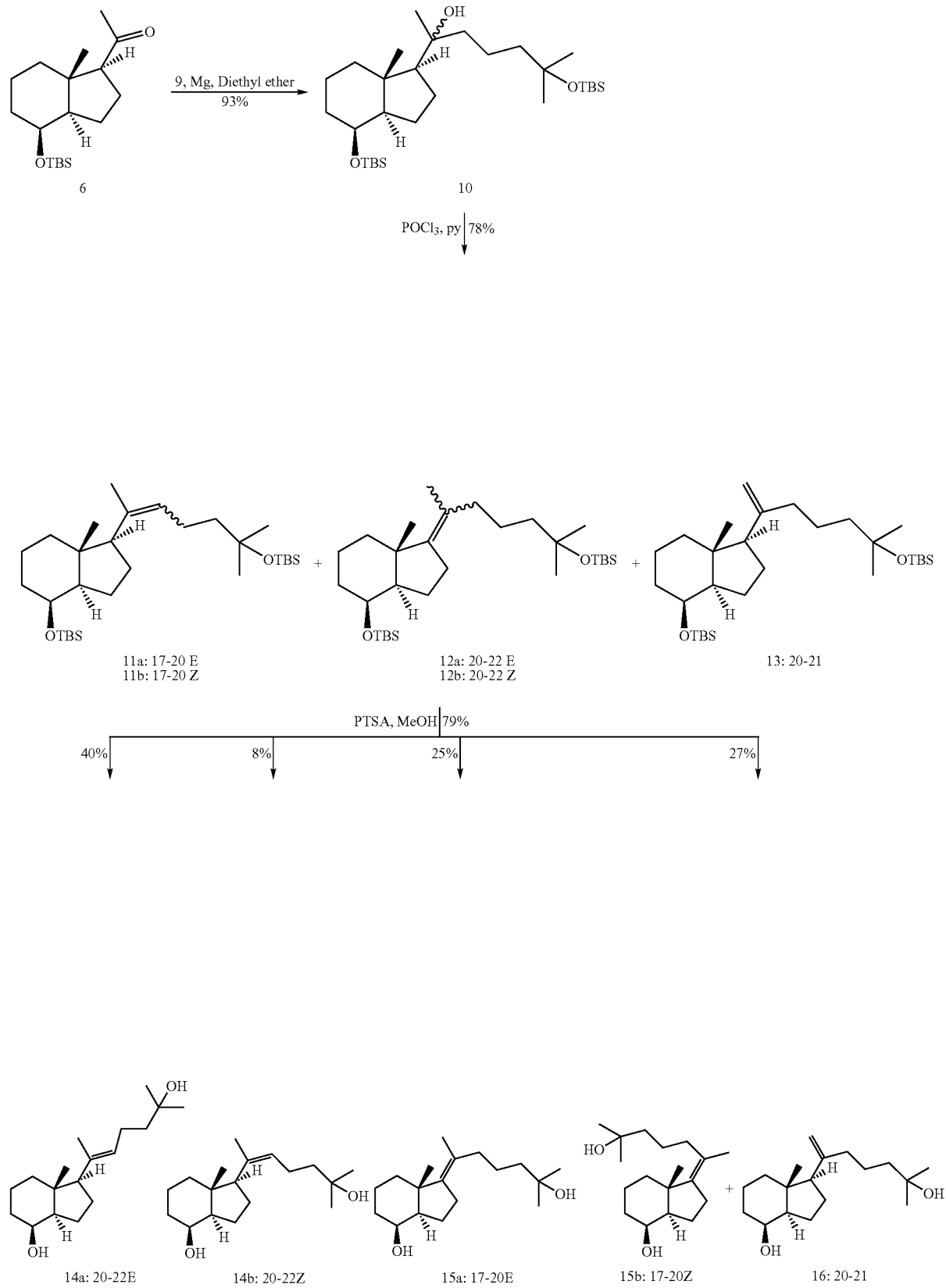
Scheme - III

Scheme - IV
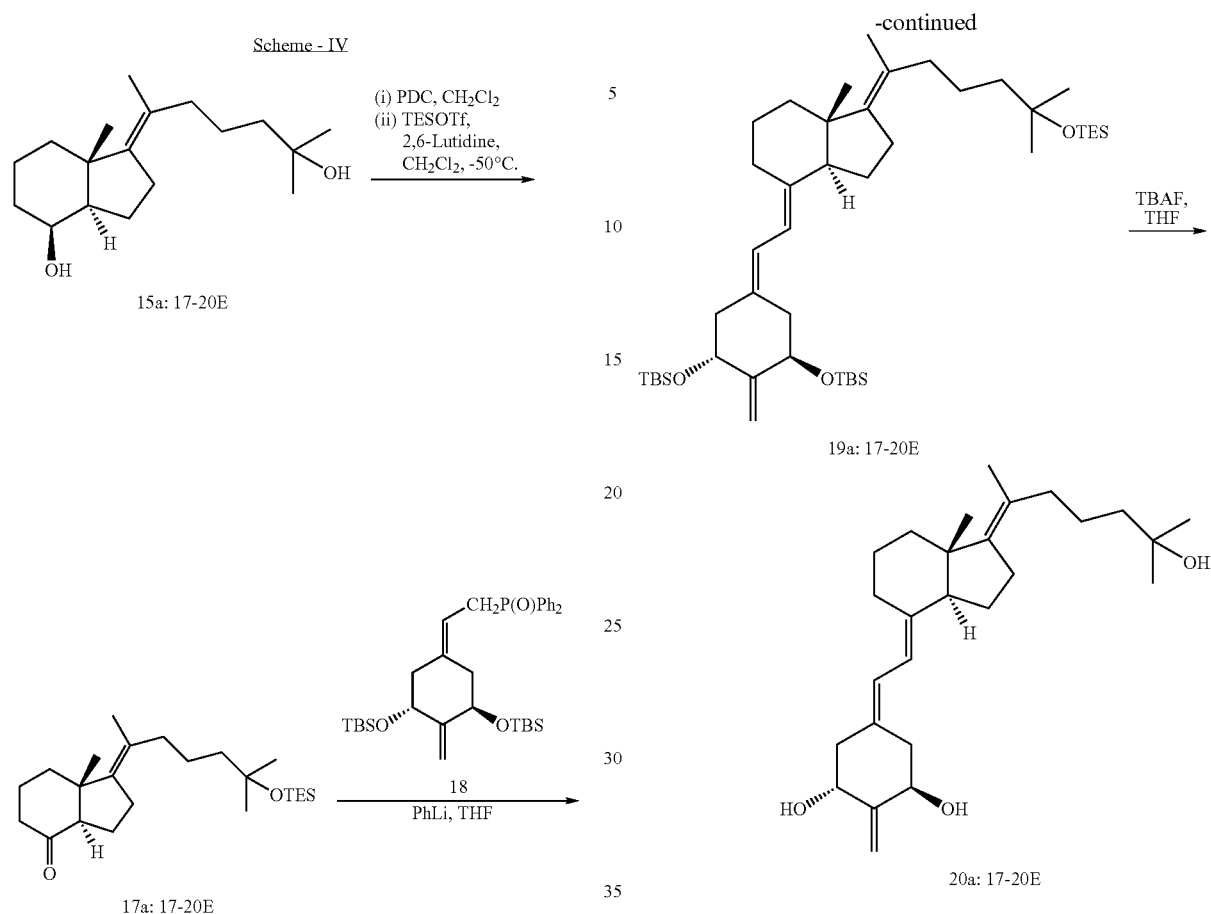
Scheme - V
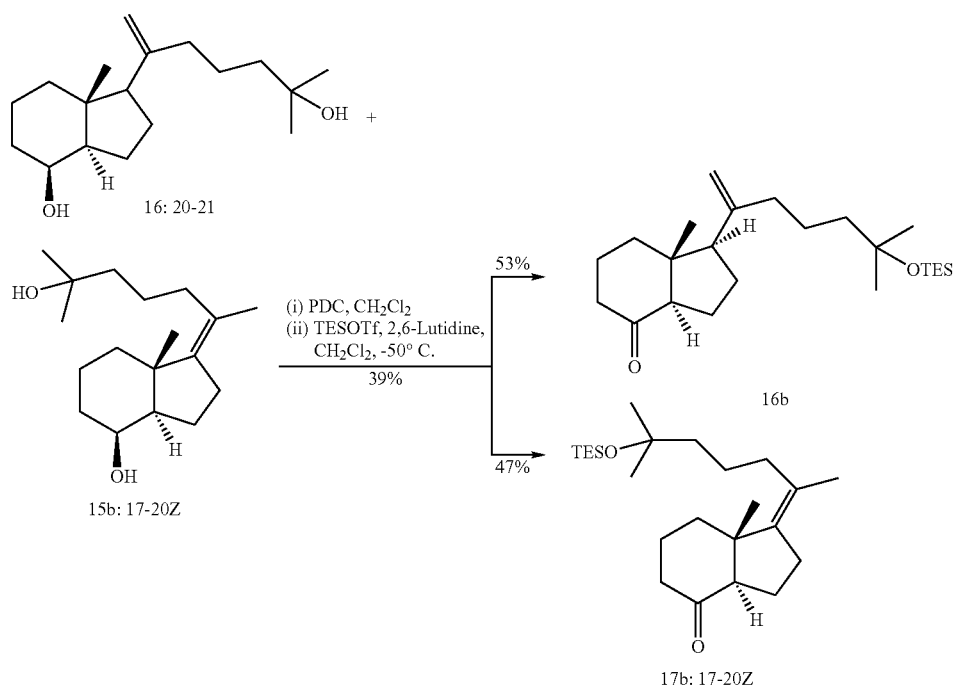

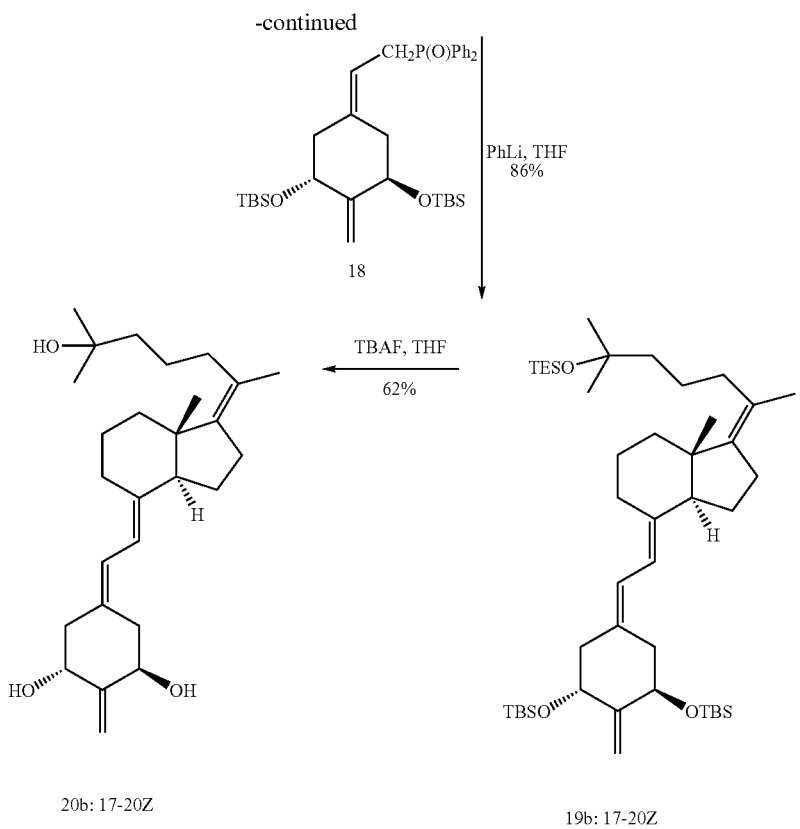

Biological Activity of 17(Z)-1α,25-Dihydroxy-17(20)-Dehydro-2-Methylene-19-Norvitamin $D_3$ The introduction of a methylene group to the 2-position, the introduction of a double bond between the 17 and 20 positions, and orienting the side chain of 1α,25-dihydroxy-19-nor-vitamin $D_3$ in its Z configuration had little or no effect on binding to the full length recombinant rat vitamin D receptor, as compared to 1α,25-dihydroxyvitamin $D_3$. The compound VIT-III bound equally well to the receptor as compared to the standard 1,25-$(OH)_2D_3$ (FIG. 1). It might be expected from these results that compound VIT-III would have equivalent biological activity. Surprisingly, however, compound VIT-III is a highly selective analog with unique biological activity.

Figure 5:
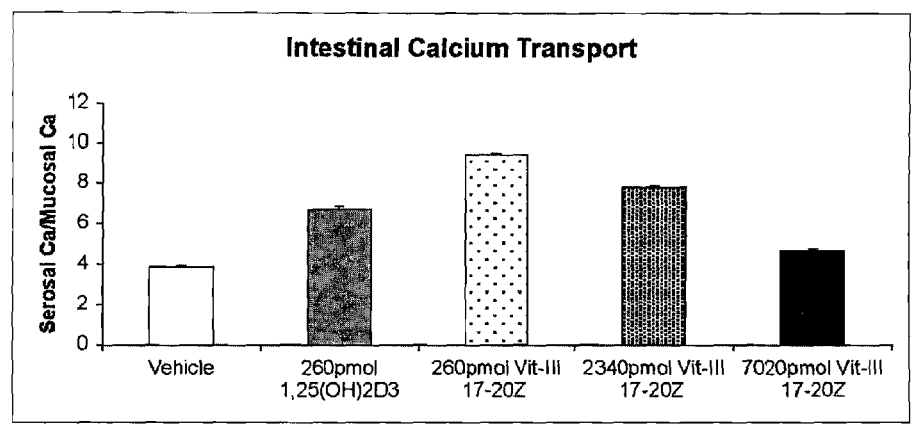

FIG. 5 shows that VIT-III has relatively high activity as compared to that of 1,25-dihydroxyvitamin $D_3$ (1,25(OH)$_2D_3$), the natural hormone, in stimulating intestinal calcium transport.

Figure 4:
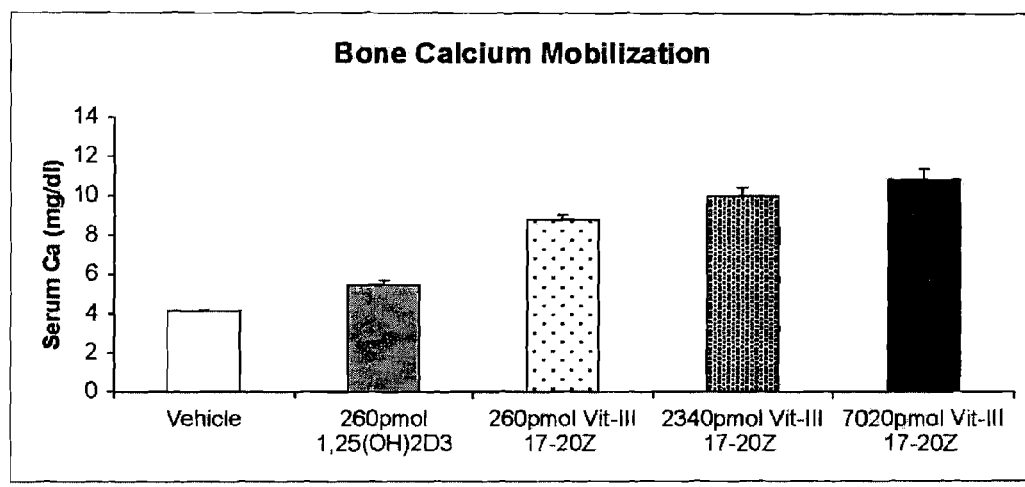

FIG. 4 demonstrates that VIT-III has relatively high bone calcium mobilization activity, as compared to 1,25$(OH)_2D_3$.

FIGS. 4-5 thus illustrate that VIT-III may be characterized as having relatively high, calcemic activity. Their preferential activity on intestinal calcium transport and calcium mobilizing activity allows the in vivo administration of these compounds for the treatment and prophylaxis of metabolic bone diseases. Because of their preferential calcemic activity on gut calcium transport and on bone, these compounds would be preferred therapeutic agents for the treatment and prophylaxis of diseases such as osteoporosis, especially low bone turnover osteoporosis, steroid induced osteoporosis, senile osteoporosis or postmenopausal osteoporosis, as well as osteomalacia and renal osteodystrophy.

Figure 2:
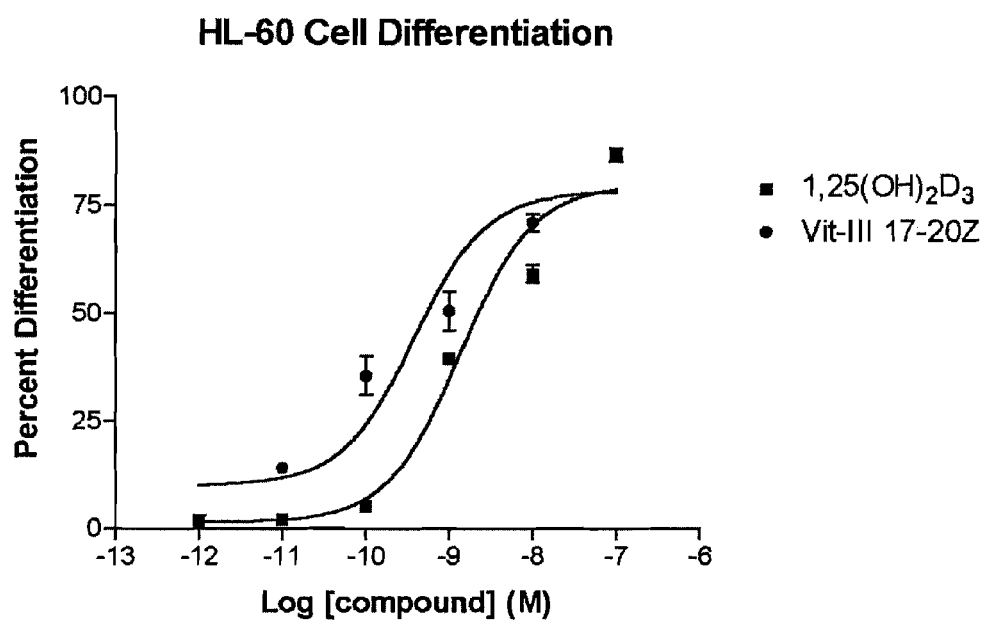

FIG. 2 illustrates that VIT-III is as potent as 1,25$(OH)_2D_3$ on HL-60 cell differentiation, making it an excellent candidate for the treatment of psoriasis and cancer, especially against leukemia, colon cancer, breast cancer, skin cancer and prostate cancer. In addition, due to its relatively high cell differentiation activity, this compound provides a therapeutic agent for the treatment of various skin conditions including wrinkles, lack of adequate dermal hydration, i.e. dry skin, lack of adequate skin firmness, i.e. slack skin, and insufficient sebum secretion. Use of this compound thus not only results in moisturizing of skin but also improves the barrier function of skin.

Figure 3:
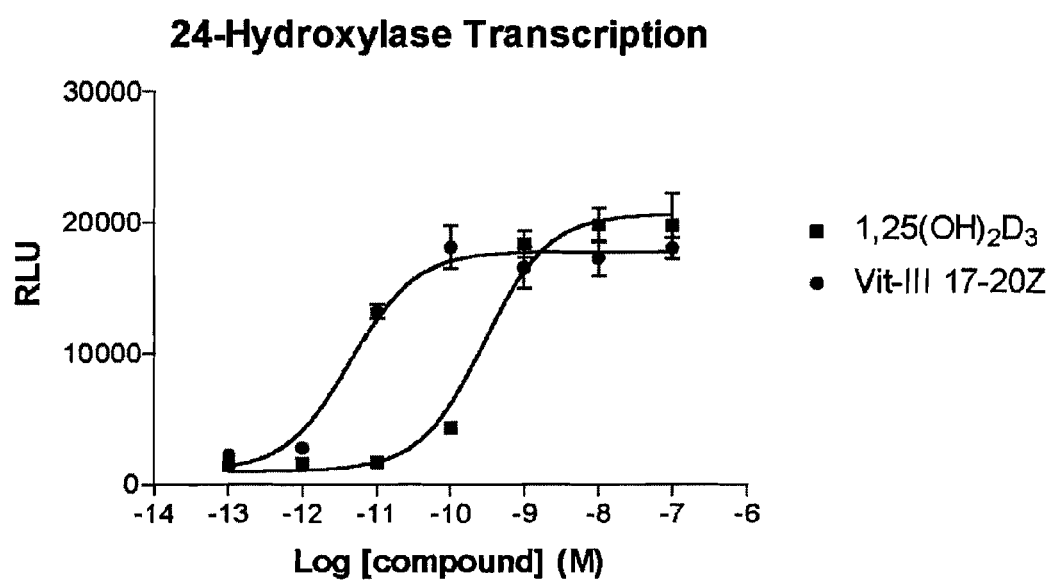

FIG. 3 illustrates that the compound VIT-III has about the same transcriptional activity as 1α,25-dihydroxyvitamin $D_3$ in bone cells. This result, together with the cell differentiation activity of FIG. 2, suggests that VIT-III will be very effective in psoriasis because it has direct cellular activity in causing cell differentiation and in suppressing cell growth. These data also indicate that VIT-III may have significant activity as an anti-cancer agent, especially against leukemia, colon cancer, breast cancer, skin cancer and prostate cancer, as well as a therapy for treating and/or preventing obesity.

The strong activity of VIT-III on HL-60 differentiation suggests it will be active in suppressing growth of parathyroid glands and in the suppression of the preproparathyroid gene. This analog having relatively high calcemic activity is also expected to be useful as a therapy to treat hypoparathyroidism since it is effective to raise blood calcium levels.

Experimental Methods

The compounds of the invention were prepared and studied using the following methods.

Vitamin D Receptor Binding

Test Material
Protein Source

Full-length recombinant rat receptor was expressed in *E. coli* BL21 (DE3) Codon Plus RIL cells and purified to homogeneity using two different column chromatography systems. The first system was a nickel affinity resin that utilizes the C-terminal histidine tag on this protein. The protein that was eluted from this resin was further purified using ion exchange chromatography (S-Sepharose Fast Flow). Aliquots of the purified protein were quick frozen in liquid nitrogen and stored at −80° C. until use. For use in binding assays, the protein was diluted in $TEDK_{50}$ (50 mM Tris, 1.5 mM EDTA, pH7.4, 5 mM DTT, 150 mM KCl) with 0.1% Chaps detergent. The receptor protein and ligand concentration was optimized such that no more than 20% of the added radiolabeled ligand was bound to the receptor.

Study Drugs

Unlabeled ligands were dissolved in ethanol and the concentrations determined using UV spectrophotometry (1,25 $(OH)_2D_3$: molar extinction coefficient=18,200 and $\lambda_{max}$=265 nm). Radiolabeled ligand ($^3$H-1,25$(OH)_2D_3$, ~159 Ci/mmole) was added in ethanol at a final concentration of 1 nM.

Assay Conditions

Radiolabeled and unlabeled ligands were added to 100 mcl of the diluted protein at a final ethanol concentration of ≦10%, mixed and incubated overnight on ice to reach binding equilibrium. The following day, 100 mcl of hydroxylapatite slurry (50%) was added to each tube and mixed at 10-minute intervals for 30 minutes. The hydroxylapaptite was collected by centrifugation and then washed three times with Tris-EDTA buffer (50 mM Tris, 1.5 mM EDTA, pH 7.4) containing 0.5% Titron X-100. After the final wash, the pellets were transferred to scintillation vials containing 4 ml of Biosafe II scintillation cocktail, mixed and placed in a scintillation counter. Total binding was determined from the tubes containing only radiolabeled ligand.

HL-60 Differentiation

Test Material
Study Drugs

The study drugs were dissolved in ethanol and the concentrations determined using UV spectrophotometry. Serial dilutions were prepared so that a range of drug concentrations could be tested without changing the final concentration of ethanol (≦0.2%) present in the cell cultures.

Cells

Human promyelocytic leukemia (HL60) cells were grown in RPMI-1640 medium containing 10% fetal bovine serum. The cells were incubated at 37° C. in the presence of 5% $CO_2$.

Assay Conditions

HL60 cells were plated at $1.2 \times 10^5$ cells/ml. Eighteen hours after plating, cells in duplicate were treated with drug. Four days later, the cells were harvested and a nitro blue tetrazolium reduction assay was performed (Collins et al., 1979; J. Exp. Med. 149:969-974). The percentage of differentiated cells was determined by counting a total of 200 cells and recording the number that contained intracellular black-blue formazan deposits. Verification of differentiation to monocytic cells was determined by measuring phagocytic activity (data not shown).

In Vitro Transcription Assay

Transcription activity was measured in ROS 17/2.8 (bone) cells that were stably transfected with a 24-hydroxylase (24Ohase) gene promoter upstream of a luciferase reporter gene (Arbour et al., 1998). Cells were given a range of doses. Sixteen hours after dosing the cells were harvested and luciferase activities were measured using a luminometer. RLU=relative luciferase units.

Antagonism was tested by adding a combination of 1,25 $(OH)_2D_3$ and the compound in the same well keeping the final ethanol concentration the same.

Intestinal Calcium Transport and Bone Calcium Mobilization

Male, weanling Sprague-Dawley rats were placed on Diet 11 (Suda et al, J. Nutr. 100:1049, 1970) (0.47% Ca)+vitamins AEK for one week followed by Diet 11 (0.02% Ca)+vitamins AEK for 3 weeks. The rats were then switched to the same diet containing 0.47% Ca for one week followed by two weeks on the same diet containing 0.02% Ca. Dose administration began during the last week on 0.02% calcium diet. Four consecutive ip doses were given approximately 24 hours apart. Twenty-four hours after the last dose, blood was collected from the severed neck and the concentration of serum calcium determined by atomic absorption spectrometry as a measure of bone calcium mobilization. The first 10 cm of the intestine was also collected for intestinal calcium transport analysis using the everted gut sac method.

Antagonism was tested by administering a combination of 1,25$(OH)_2D_3$ and the compound to the animal simultaneously.

Interpretation of Data

VDR bindings, HL60 cell differentiation, and transcription activity. VIT-III ($K_i$=5.0×10$^{-11}$M) is equivalent to the natural hormone 1α,25-dihydroxyvitamin $D_3$ ($K_i$=4.9×10$^{-11}$M) in its ability to compete with [$^3$H]-1,25$(OH)_2D_3$ for binding to the full-length recombinant rat vitamin D receptor (FIG. 1). VIT-III is also significantly higher ($EC_{50}$=3.7×10$^{-10}$M) in its ability (efficacy or potency) to promote HL60 differentiation as compared to 1α,25-dihydroxyvitamin $D_3$ ($EC_{50}$=1.3×10$^{-9}$ M) (See FIG. 2). Also, compound VIT-III ($EC_{50}$=4.4×10$^{-12}$ M) has greater transcriptional activity in bone cells than 1α,25-dihydroxyvitamin $D_3$ ($EC_{50}$=2.9×10$^{-10}$M) (See FIG. 3). These results suggest that VIT-III will be very effective in psoriasis because it has direct cellular activity in causing cell differentiation and in suppressing cell growth. These data also indicate that VIT-III will have significant activity as an anticancer agent, especially against leukemia, colon cancer, breast cancer, skin cancer and prostate cancer, as well as against skin conditions such as dry skin (lack of dermal hydration), undue skin slackness (insufficient skin firmness), insufficient sebum secretion and wrinkles. It would also be expected to be very active in suppressing secondary hyperparathyroidism.

Calcium mobilization from bone and intestinal calcium absorption in vitamin D-deficient animals. Using vitamin D-deficient rats on a low calcium diet (0.02%), the activities of VIT-III and 1,25$(OH)_2D_3$ in intestine and bone were tested.

As expected, the native hormone ($1,25(OH)_2D_3$) increased serum calcium levels at the dosage tested (FIG. 4). FIG. 4 also shows that VIT-III has significantly greater activity in mobilizing calcium from bone than $1,25(OH)_2D_3$. Administration of VIT-III at 260 pmol/day for 4 consecutive days resulted in significant mobilization of bone calcium, and increasing the amount of VIT-III to 2340 pmol/day and then to 7020 pmol/day also increased the effect to provide progressively increasing serum calcium levels well above the effects seen with $1,25(OH)_2D_3$.

Intestinal calcium transport was evaluated in the same groups of animals using the everted gut sac method (FIG. 5). These results show that the compound VIT-III promotes a significant increase in intestinal calcium transport activity when administered at 260 pmol/day, 2340 pmol/day or 7020 pmol/day, as compared to $1,25(OH)_2D_3$ at the 260 pmol/day dose. Thus, it may be concluded that VIT-III has significant intestinal calcium transport activity at the tested doses.

These results illustrate that VIT-III is an excellent candidate for numerous human therapies as described herein, and that it may be particularly useful in a number of circumstances such as suppression of secondary hyperparathyroidism of renal osteodystrophy, autoimmune diseases, cancer, and psoriasis. VIT-III is an excellent candidate for treating psoriasis because: (1) it has significant VDR binding, transcription activity and cellular differentiation activity; (2) it is devoid of hypercalcemic liability unlike $1,25(OH)_2D_3$; and (3) it is easily synthesized. Since VIT-III has significant binding activity to the vitamin D receptor, but has little ability to raise blood serum calcium, it may also be particularly useful for the treatment of secondary hyperparathyroidism of renal osteodystrophy.

These data also indicate that the compound VIT-III of the invention may be especially suited for treatment and prophylaxis of human disorders which are characterized by an imbalance in the immune system, e.g. in autoimmune diseases, including multiple sclerosis, lupus, diabetes mellitus, host versus graft rejection, and rejection of organ transplants; and additionally for the treatment of inflammatory diseases, such as rheumatoid arthritis, asthma, and inflammatory bowel diseases such as celiac disease, ulcerative colitis and Crohn's disease. Acne, alopecia and hypertension are other conditions which may be treated with the compound VIT-III of the invention.

The compounds of the invention of formula I, and particularly formula Ia, are also useful in preventing or treating obesity, inhibiting adipocyte differentiations, inhibiting SCD-1 gene transcription, and/or reducing body fat in animal subjects. Therefore, in some embodiments, a method of preventing or treating obesity, inhibiting adipocyte differentiations, inhibiting SCD-1 gene transcription, and/or reducing body fat in an animal subject includes administering to the animal subject, an effective amount of one or more of the compounds or a pharmaceutical composition that includes one or more of the compounds of formula I. Administration of one or more of the compounds or the pharmaceutical compositions to the subject inhibits adipocyte differentiation, inhibits gene transcription, and/or reduces body fat in the animal subject. The animal may be a human, a domestic animal such as a dog or a cat, or an agricultural animal, especially those that provide meat for human consumption, such as fowl like chickens, turkeys, pheasant or quail, as well as bovine, ovine, caprine, or porcine animals.

For prevention and/or treatment purposes, the compounds of this invention defined by formula I and Ia may be formulated for pharmaceutical applications as a solution in innocuous solvents, or as an emulsion, suspension or dispersion in suitable solvents or carriers, or as pills, tablets or capsules, together with solid carriers, according to conventional methods known in the art. Any such formulations may also contain other pharmaceutically-acceptable and non-toxic excipients such as stabilizers, anti-oxidants, binders, coloring agents or emulsifying or taste-modifying agents.

The compounds of formula I and particularly VIT-III of formula Ia, may be administered orally, topically, parenterally, rectally, nasally, sublingually, or transdermally. The compound is advantageously administered by injection or by intravenous infusion or suitable sterile solutions, or in the form of liquid or solid doses via the alimentary canal, or in the form of creams, ointments, patches, or similar vehicles suitable for transdermal applications. A dose of from 0.01 µg to 1000 µg per day of the compounds I, particularly VIT-III, preferably from about 0.1 µg to about 500 µg per day, is appropriate for prevention and/or treatment purposes, such dose being adjusted according to the disease to be treated, its severity and the response of the subject as is well understood in the art. Since the compound exhibits specificity of action, each may be suitably administered alone, or together with graded doses of another active vitamin D compound—e.g. $1\alpha$-hydroxyvitamin $D_2$ or $D_3$, or $1\alpha,25$-dihydroxyvitamin $D_3$—in situations where different degrees of bone mineral mobilization and calcium transport stimulation is found to be advantageous.

Compositions for use in the above-mentioned treatments comprise an effective amount of the compounds I, particularly VIT-III, as defined by the above formula I and Ia as the active ingredient, and a suitable carrier. An effective amount of such compound for use in accordance with this invention is from about 0.01 µg to about 1000 µg per gm of composition, preferably from about 0.1 µg to about 500 µg per gram of composition, and may be administered topically, transdermally, orally, rectally, nasally, sublingually or parenterally in dosages of from about 0.01 µg/day to about 1000 µg/day, and preferably from about 0.1 µg/day to about 500 µg/day.

The compounds I, particularly VIT-III, may be formulated as creams, lotions, ointments, topical patches, pills, capsules or tablets, suppositories, aerosols, or in liquid form as solutions, emulsions, dispersions, or suspensions in pharmaceutically innocuous and acceptable solvent or oils, and such preparations may contain in addition other pharmaceutically innocuous or beneficial components, such as stabilizers, antioxidants, emulsifiers, coloring agents, binders or taste-modifying agents.

The compounds I, particularly VIT-III, may be advantageously administered in amounts sufficient to effect the differentiation of promyelocytes to normal macrophages. Dosages as described above are suitable, it being understood that the amounts given are to be adjusted in accordance with the severity of the disease, and the condition and response of the subject as is well understood in the art.

The formulations of the present invention comprise an active ingredient in association with a pharmaceutically acceptable carrier therefore and optionally other therapeutic ingredients. The carrier must be "acceptable" in the sense of being compatible with the other ingredients of the formulations and not deleterious to the recipient thereof.

Formulations of the present invention suitable for oral administration may be in the form of discrete units as capsules, sachets, tablets or lozenges, each containing a predetermined amount of the active ingredient; in the form of a powder or granules; in the form of a solution or a suspension in an aqueous liquid or non-aqueous liquid; or in the form of an oil-in-water emulsion or a water-in-oil emulsion.

Formulations for rectal administration may be in the form of a suppository incorporating the active ingredient and carrier such as cocoa butter, or in the form of an enema.

Formulations suitable for parenteral administration conveniently comprise a sterile oily or aqueous preparation of the active ingredient which is preferably isotonic with the blood of the recipient.

Formulations suitable for topical administration include liquid or semi-liquid preparations such as liniments, lotions, applicants, oil-in-water or water-in-oil emulsions such as creams, ointments or pastes; or solutions or suspensions such as drops; or as sprays.

For nasal administration, inhalation of powder, self-propelling or spray formulations, dispensed with a spray can, a nebulizer or an atomizer can be used. The formulations, when dispensed, preferably have a particle size in the range of 10 to 100μ.

The formulations may conveniently be presented in dosage unit form and may be prepared by any of the methods well known in the art of pharmacy. By the term "dosage unit" is meant a unitary, i.e. a single dose which is capable of being administered to a patient as a physically and chemically stable unit dose comprising either the active ingredient as such or a mixture of it with solid or liquid pharmaceutical diluents or carriers.

We claim:

1. A method of treating obesity of an animal, inhibiting adipocyte differentiation, inhibiting SCD-1 gene transcription, and/or reducing body fat in an animal comprising administering to an animal in need thereof an effective amount of a 17(20)-dehydro vitamin D compound having the formula:

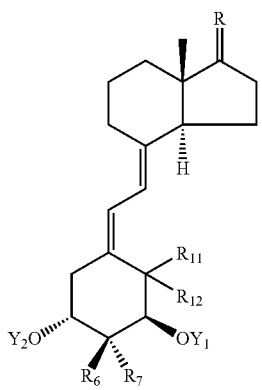

where $Y_1$ and $Y_2$, which may be the same or different, are each selected from the group consisting of hydrogen and a hydroxy-protecting group, where $R_{11}$ and $R_{12}$ are each hydrogen, where $R_6$ and $R_7$, which may be the same or different, are each selected from the group consisting of hydrogen, alkyl, hydroxyalkyl, fluoroalkyl, hydroxy and alkoxy, or $R_6$ and $R_7$ when taken together may represent the group —$(CH_2)_x$— where x is an integer from 2 to 5, or $R_6$ and $R_7$ when taken together may represent the group =$CR_8R_9$ where $R_8$ and $R_9$, which may be the same or different, are each selected from the group consisting of hydrogen, alkyl, hydroxyalkyl, fluoroalkyl, hydroxy and alkoxy, or when taken together $R_8$ and $R_9$ may represent the group —$(CH_2)_x$— where x is an integer from 2 to 5, and where the group R represents a side chain represented by the structure

where the side chain and 17-ene double bond is in the Z configuration and where Z in the above side chain structure is selected from Y, —OY, —$CH_2OY$, —C≡CY and —CH═CHY, where the double bond in the side chain may have the cis or trans geometry, and where Y is selected from hydrogen, —$COR^5$ and a radical of the structure:

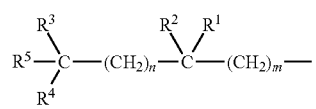

where m and n, independently, represent the integers from 0 to 5, where $R^1$ is selected from hydrogen, deuterium, hydroxy, protected hydroxy, fluoro, trifluoromethyl, and $C_{1-5}$-alkyl, which may be straight chain or branched and, optionally, bear a hydroxy or protected-hydroxy substituent, and where each of $R^2$, $R^3$, and $R^4$, independently, is selected from deuterium, deuteroalkyl, hydrogen, fluoro, trifluoromethyl and $C_{1-5}$ alkyl, which may be straight-chain or branched, and optionally, bear a hydroxy or protected-hydroxy substituent, and where $R^1$ and $R^2$, taken together, represent an oxo group, or an alkylidene group having a general formula $C_kH_{2k}$— where k is an integer, the group =$CR^2R^3$, or the group —$(CH_2)_p$—, where p is an integer from 2 to 5, and where $R^3$ and $R^4$, taken together, represent an oxo group, or the group —$(CH_2)_q$—, where q is an integer from 2 to 5, and where $R^5$ represents hydrogen, hydroxy, protected hydroxy, or $C_{1-5}$ alkyl and wherein any of the CH— groups at positions 20, 22, or 23 in the side chain may be replaced by a nitrogen atom, or where any of the groups —$CH(CH_3)$—, —$(CH_2)_m$—, —$CR_1R_2$— or —$(CH_2)_n$— at positions 20, 22, and 23, respectively, may be replaced by an oxygen or sulfur atom.

2. The method of claim 1 wherein the vitamin D compound is administered orally.

3. The method of claim 1 wherein the vitamin D compound is administered parenterally.

4. The method of claim 1 wherein the vitamin D compound is administered transdermally.

5. The method of claim 1 wherein the vitamin D compound is administered in a dosage of from about 0.01 μg/date to about 1000 μg/day.

6. The method of claim 1 wherein the animal is a human.

7. The method of claim 1 wherein the animal is a domestic animal.

8. The method of claim 1 wherein the animal is an agricultural animal.

9. A method of treating obesity of an animal, inhibiting adipocyte differentiation, inhibiting SCD-1 gene transcription, and/or reducing body fat in an animal comprising administering to an animal in need thereof an effective amount of 17(Z)-1α,25-dihydroxy-17(20)-dehydro-2-methylene-19-nor-vitamin $D_3$ having the formula:

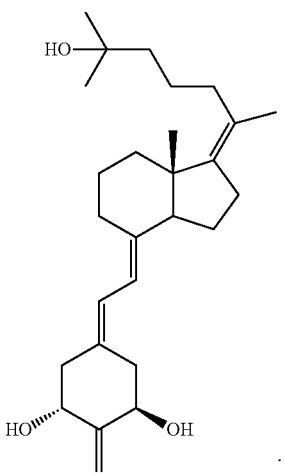

10. The method of claim 9 wherein 17(Z)-1α,25-dihydroxy-17(20)-dehydro-2-methylene-19-nor-vitamin $D_3$ is administered orally.

11. The method of claim 9 wherein 17(Z)-1α,25-dihydroxy-17(20)-dehydro-2-methylene-19-nor-vitamin $D_3$ is administered parenterally.

12. The method of claim 9 wherein 17(Z)-1α,25-dihydroxy-17(20)-dehydro-2-methylene-19-nor-vitamin $D_3$ is administered transdermally.

13. The method of claim 9 wherein 17(Z)-1α,25-dihydroxy-17(20)-dehydro-2-methylene-19-nor-vitamin $D_3$ is administered in a dosage of from about 0.01 μg/day to about 1000 μg/day.

14. The method of claim 9 wherein the animal is a human.

15. The method of claim 9 wherein the animal is a domestic animal.

16. The method of claim 9 wherein the animal is an agricultural animal.

* * * * *